US009296824B2

(12) United States Patent
Yan

(10) Patent No.: US 9,296,824 B2
(45) Date of Patent: Mar. 29, 2016

(54) METHODS FOR TREATING AND PREVENTING MULTIPLE SCLEROSIS

(75) Inventor: Shi Du Yan, Tenafly, NJ (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 1615 days.

(21) Appl. No.: 12/598,525

(22) PCT Filed: May 1, 2008

(86) PCT No.: PCT/US2008/062158
§ 371 (c)(1),
(2), (4) Date: Nov. 2, 2009

(87) PCT Pub. No.: WO2008/134767
PCT Pub. Date: Nov. 6, 2008

(65) Prior Publication Data
US 2010/0136002 A1    Jun. 3, 2010

Related U.S. Application Data

(60) Provisional application No. 60/915,127, filed on May 1, 2007.

(51) Int. Cl.
*A61K 39/395*    (2006.01)
*C07K 16/40*    (2006.01)
*C12N 15/113*    (2010.01)
*A61K 48/00*    (2006.01)

(52) U.S. Cl.
CPC ............ *C07K 16/40* (2013.01); *C12N 15/1137* (2013.01); *C12Y 301/05001* (2013.01); *A61K 48/00* (2013.01); *C12N 2310/14* (2013.01)

(58) Field of Classification Search
CPC .... A61K 48/00; C07K 16/40; C12N 15/1137; C12N 2310/14; C12Y 301/05001
USPC ......... 424/133.1, 136.1, 152.1, 172.1; 435/29
See application file for complete search history.

(56) References Cited

U.S. PATENT DOCUMENTS

2003/0017985 A1    1/2003    Taylor et al.

OTHER PUBLICATIONS

Lam-Tse et al., Springer Semin Immunopathol., vol. 24, pp. 297-321, 2002.*
't Hart et al., The Lancet Neurology, vol. 3, pp. 588-597, 2004.*
Baker et al., Multiple Sclerosis Journal, vol. 17, pp. 647-657, 2011.*
"Autoimmunity" entry, Wikipedia.org, pp. 1-15, dowloaded on Jun. 30, 2014.*
Kies, Advances in experimental medicine and biology, vol. 100, pp. 277-288, 1978.*
Sriram et al., Ann Neurol., vol. 58, pp. 939-945, 2005.*
Holmoy et al., Acta Neurol. Scand., vol. 115 (Suppl. 187), pp. 39-45, 2007.*
Handel et al., Eur. J. Clin. Invest., vol. 41, pp. 1254-1258, 2011.*
Butcher, B. et al., p47 GTPases Regulate Toxoplasma gondii Survival in Activated Macrophages, journal, Jun. 2005, pp. 3278-3286, vol. 73, No. 6, American Society for Microbiology, United States.
Chu, C. et al., Failure to Suppress the Expansion of the Activated CD4 T Cell Population in Interferon y-deficient Mice Leads to Exacerbation of Experimental Autoimmune Encephalomyelitis, journal, Jul. 3, 2000, pp. 123-128, vol. 192, No. 1, The Rockefeller University Press, United States.
Collazo, C. et al., Inactivation of LRG-47 and IRG-47 Reveals a Family of Interferon y-inducible GEnes with Essential, Pathogen-specific Roles in Resistance to Infection, journal, Jul. 16, 2001, pp. 181-187, vol. 194, No. 2, United States.
Dalton, D. et al., Interferon y Eliminates Responding CD4 T Cells during Mycobacterial Infection by Inducing Apoptosis of Acted CD4 T Cells, journal, Jul. 3, 2000, pp. 117-122, vol. 192, No. 1, The Rockefeller University Press, United States.
Feng, C. et al., Mice Deficient in LRG-47 Display Increased Susceptibility to Mycobaterial Infection Associated with the Induction of Lymphopenia, journal, The Journal of Immunology, Oct. 30, 2003, pp. 1163-1168, The American Association of Immunologists, Inc., United States.
Fuiterrez, M. et al., Autophagy IS a Defense Mechanism Inhibiting BCG and Mycobacterium tuberculosis Survival in Infected Macrophages, journal, Dec. 17, 2004, pp. 753-766, vol. 119, Cell Press, United States.
Macmicking, J. et al., Immune Control of Tuberculosis by IFN-y-Inducible LRG-47, journal, Oct. 24, 2003, pp. 654-659, vol. 302, United States.
Macmicking, J., IFN-inducible GTPases and immunity to intracellular pathogens, journal, Nov. 2004, pp. 601-609, vol. 25, No. 11, Elsevier Ltd., United States.
Macmicking, J., Immune control of phagosomal bacteria by p47 GTPases, journal, Jan. 2005, pp. 74-82, Elsevier Ltd., United States.
Martens, S. et al., Mechanisms Regulating the Positioning of Mouse p47 Resistance GTPases LRG-47 and IIGP1 on Cellular Membranes: Retargeting to Plasma Membrane Induced by Phagocytosis, journal, The Journal of Immunology, May 18, 2004, pp. 2594-2606, The American Association of Immunologists, Inc., United States.

(Continued)

*Primary Examiner* — Jeffrey Stucker
*Assistant Examiner* — Stephen Gucker
(74) *Attorney, Agent, or Firm* — Beusse Wolter Sanks & Maire PLLC; Judith A. Evans

(57) ABSTRACT

We have discovered that LRG-47 (also called p47 GTPase), plays a central role in the pathogenesis of multiple sclerosis, and that inhibition of LRG-47 activity by anti-LRG-47 antibodies or of LRG-47 expression by siRNA dramatically reduce the pathology and symptoms of multiple sclerosis. Certain embodiments of the invention are directed to the therapeutic use of anti-LRG-47 antibodies (mouse or rabbit or other antibodies that are humanized or human antibodies to LRG-47, preferably antibodies made against human LRG-47) or siRNA or antisense nucleotides that specifically hybridize with the gene or mRNA or cDNA encoding human LRG-47 to treat or prevent multiple sclerosis and other autoimmune diseases that are T-cell-mediated. Other embodiments are directed to methods for the diagnosis of multiple sclerosis or to determining the aggressiveness of multiple sclerosis by determining the amount of human LRG-47 or LRG-47 mRNA in a biological sample from the patient.

4 Claims, 15 Drawing Sheets

(56) References Cited

OTHER PUBLICATIONS

O'Conner, R. et al., Infection-induced apoptosis deletes bystander CD4* + T Cells: a mechanism for suppression of autoimmunity during BCG infection, journal, Dec. 14, 2004, pp. 93-100, Elsevier, Ltd., United States.

Refaeli, Y. et al., Interferon y is Required for Activation-induced Death of T Lymphocytes, journal, Oct. 7, 2002, pp. 999-1005, vol. 196, No. 7, The Rockefeller University Press, United States.

Santiago, H. et al., Mice Deficient in LRG-47 Display Enhanced Susceptibility to Trypanosoma cruzi Infection Associated with Defective Hemopoiesis and Intracellular Control of Parasite Growth, journal, The Journal of Immunology, Sep. 23, 2005, pp. 8165-8172, The American Association of Immunologists, Inc., United States.

Sorace, J. et al., Identification of an endotoxin and IFN-inducible cDNA: possible identification of a novel protein family, journal, Journal Leukocyte Biology, May 4, 1995, pp. 477-484, vol. 58.

Taylor, G. et al., Identification of a Noval GTPase, the Inducibly Expressed GTPase, That Accumulates in Response to Interferon y, journal, The Journal of Biological Chemistry, May 31, 1996, pp. 20399-20405, vol. 271, No. 34, United States.

Taylor, G. et al., P47 GTPases: Regulators of Immunity to Intracellular Pathogens, journal, Feb. 2004, pp. 100-109, vol. 4, Nature Publishing Group, United States.

Xu, H. et al., Genetic deficiency of Irgm1 (LRG-47) suppresses inductin of experimental autoimmune encephalomyelitis by promoting apoptosis of activated CD4* + T cells, journal, The FASEB Journal, May 2010, pp. 1-10, vol. 24, United States.

Yan, S. et al., Suppression of experimental autoimmune encephalomyelitis by selective blockade of encephalitogenic T-cell infiltration of the central nervous system, journal, Feb. 18, 2003, pp. 287-293, vol. 9, No. 3, Nature Publishing Group, United States.

Zhang, Y. et al., Regulation of innate and adaptive immune responses by MAP kinase phosphatase 5, journal, Aug. 12, 2004, pp. 793-797, vol. 430, Nature Publishing Group, United States.

Sorace et al. Identification of an endotoxin and IFN-inducible cDNA: possible identification of a novel protein family. J. Leukoc. Biol., 1995, vol. 58(4), p. 477-484. Abstract; p. 480, col. 2; and p. 481, col. 2, last para.

LeClaire et al. Characterization and use of monoclonal and polyclonal antibodies against the mouse interferon-gamma receptor. J. Leukoc.Biol., 1992, vol. 51(5), p. 507-516. Abstract.

International Search Report and Written Opinion, WO 2008/134767 A3, Sep. 26, 2008, pp. 1-12.

* cited by examiner

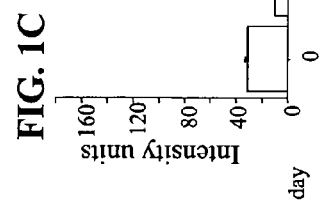
FIG. 1A
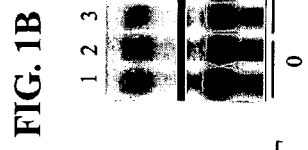
FIG. 1B
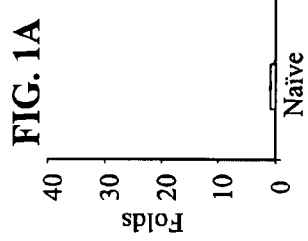
FIG. 1D
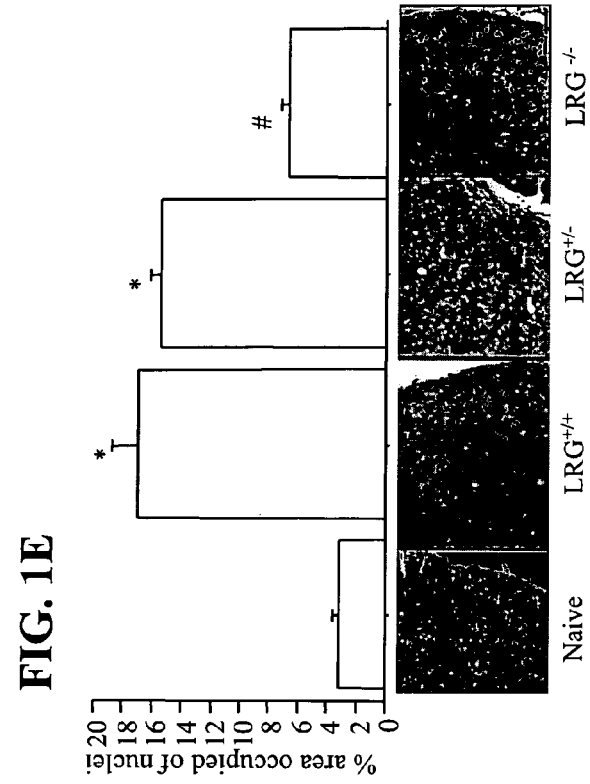
FIG. 1C
FIG. 1E
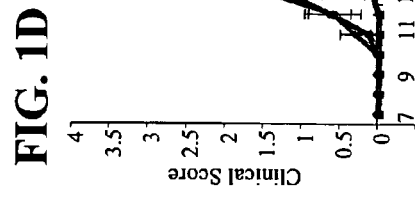

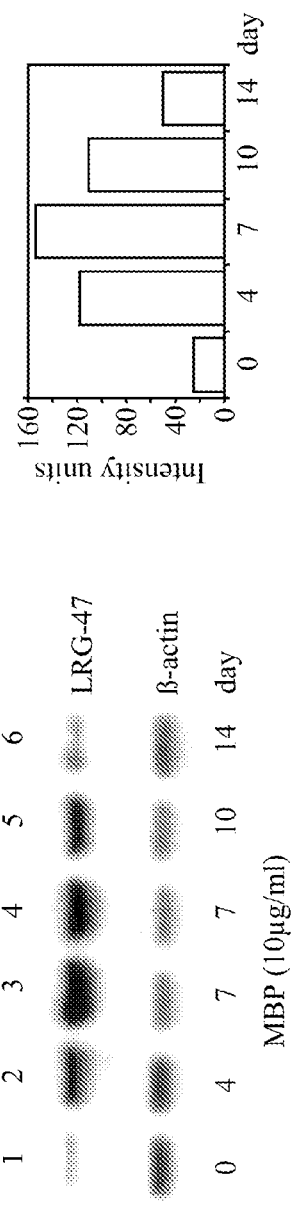
FIG. 3A
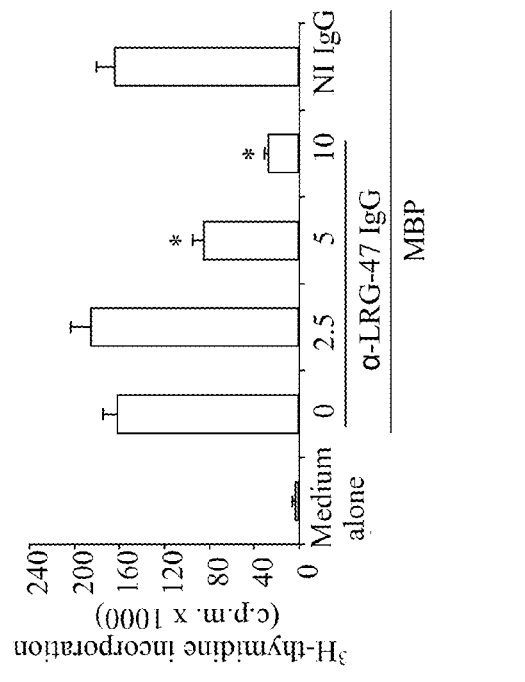
FIG. 3D
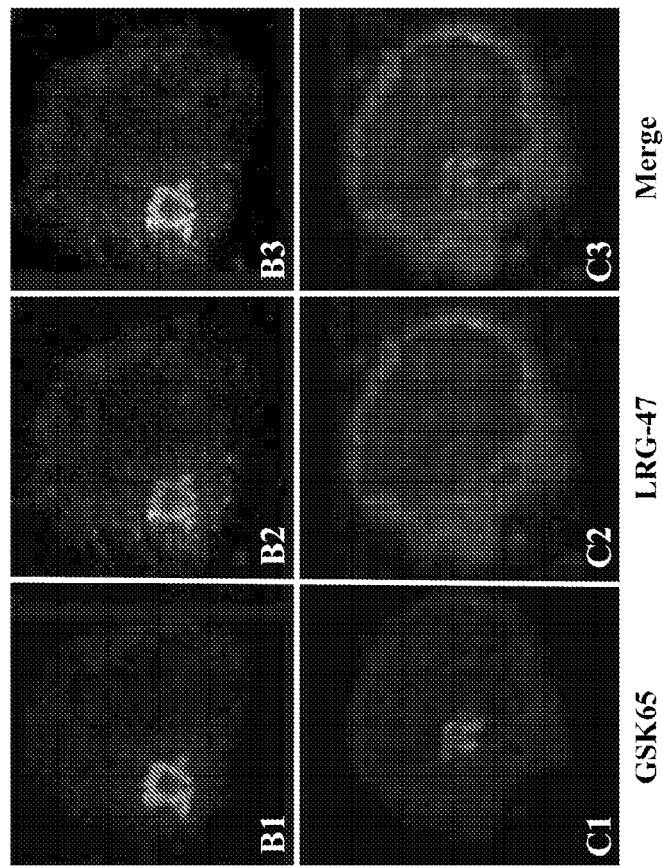
FIG. 3B-C

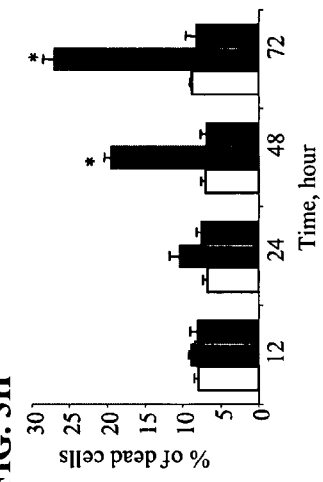
FIG. 3F
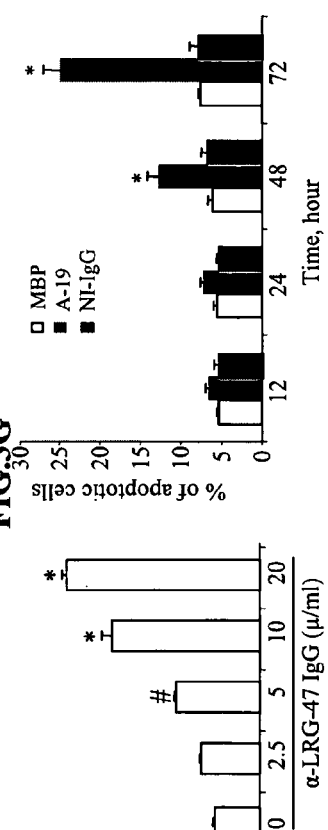
FIG. 3G
FIG. 3H
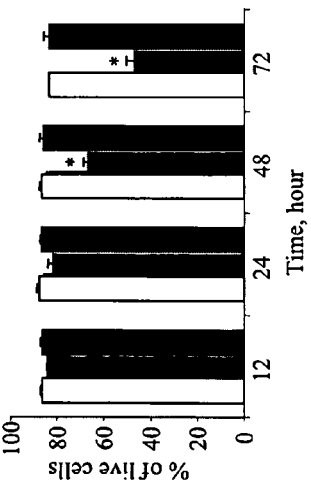
FIG. 3I

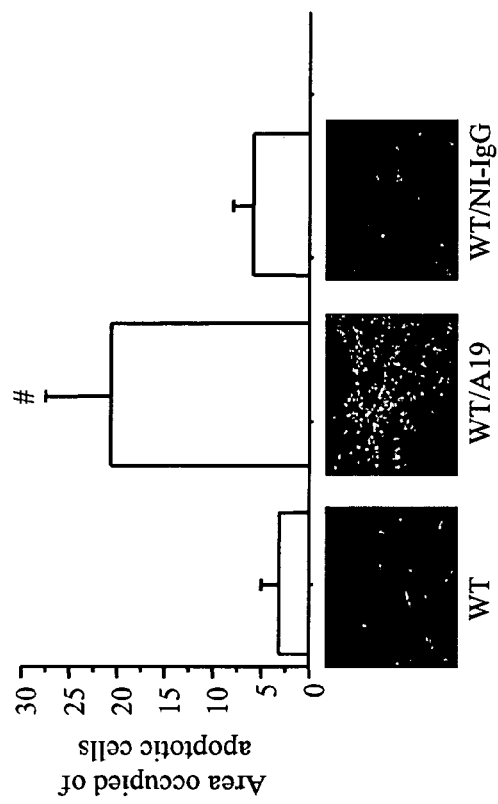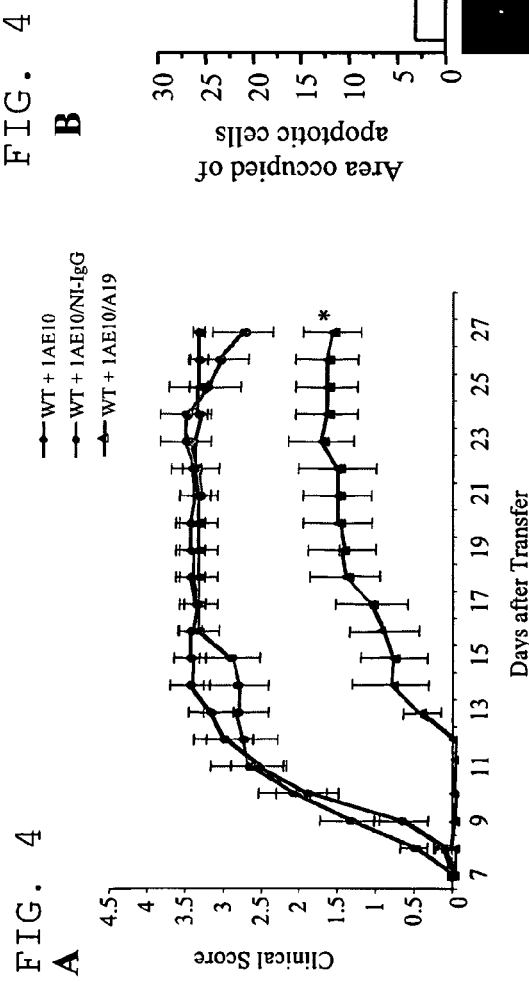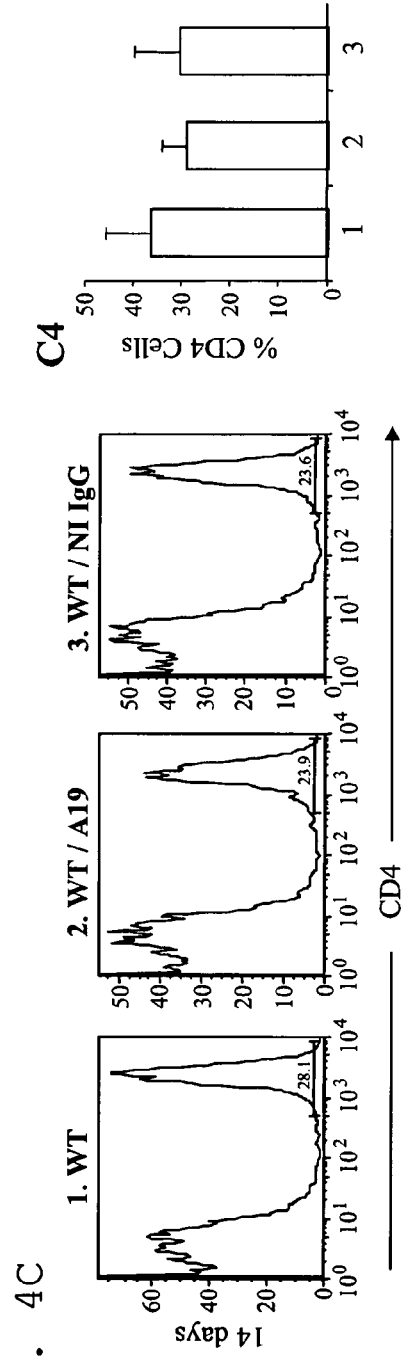
FIG. 4A
FIG. 4B
FIG. 4C

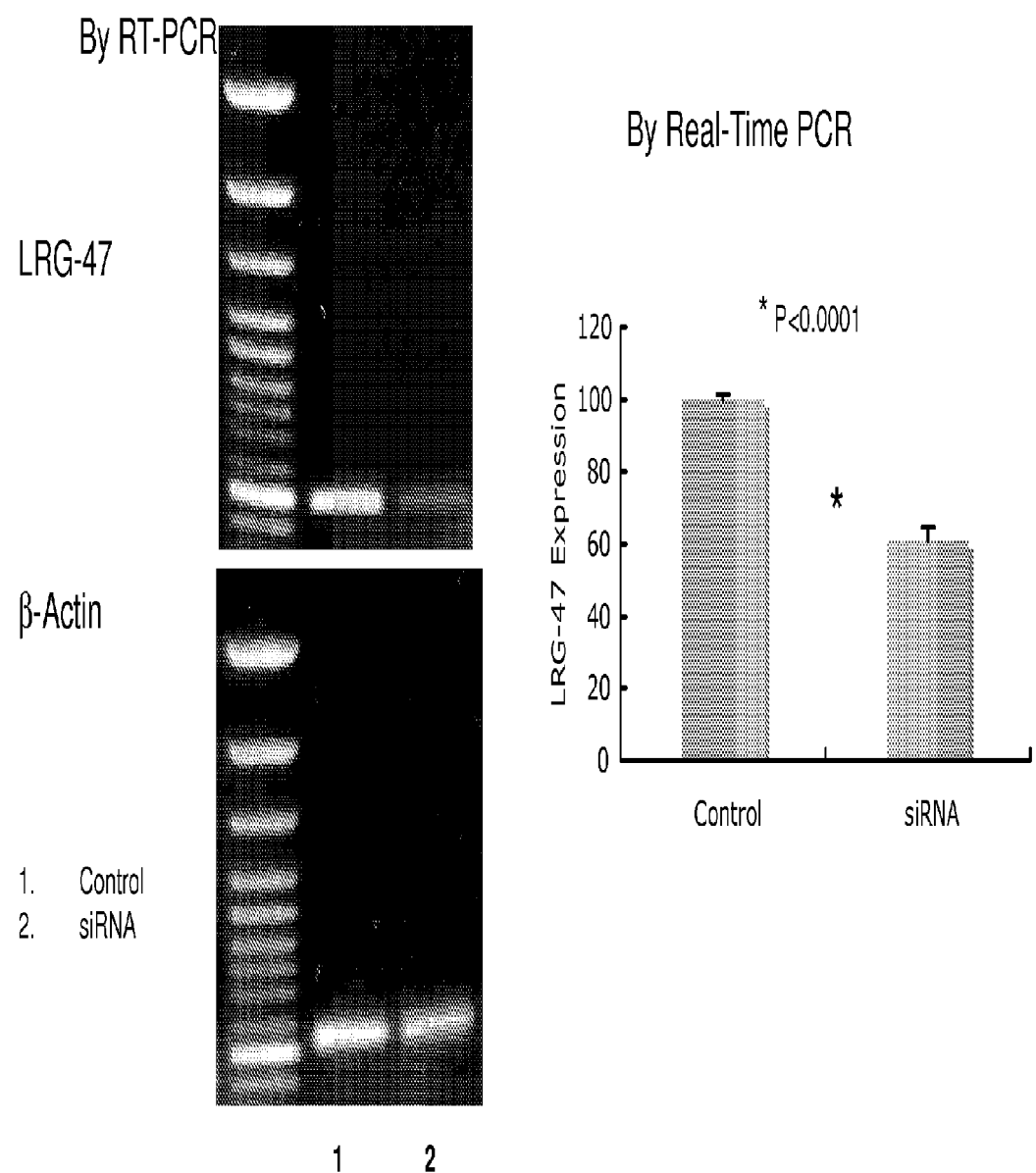

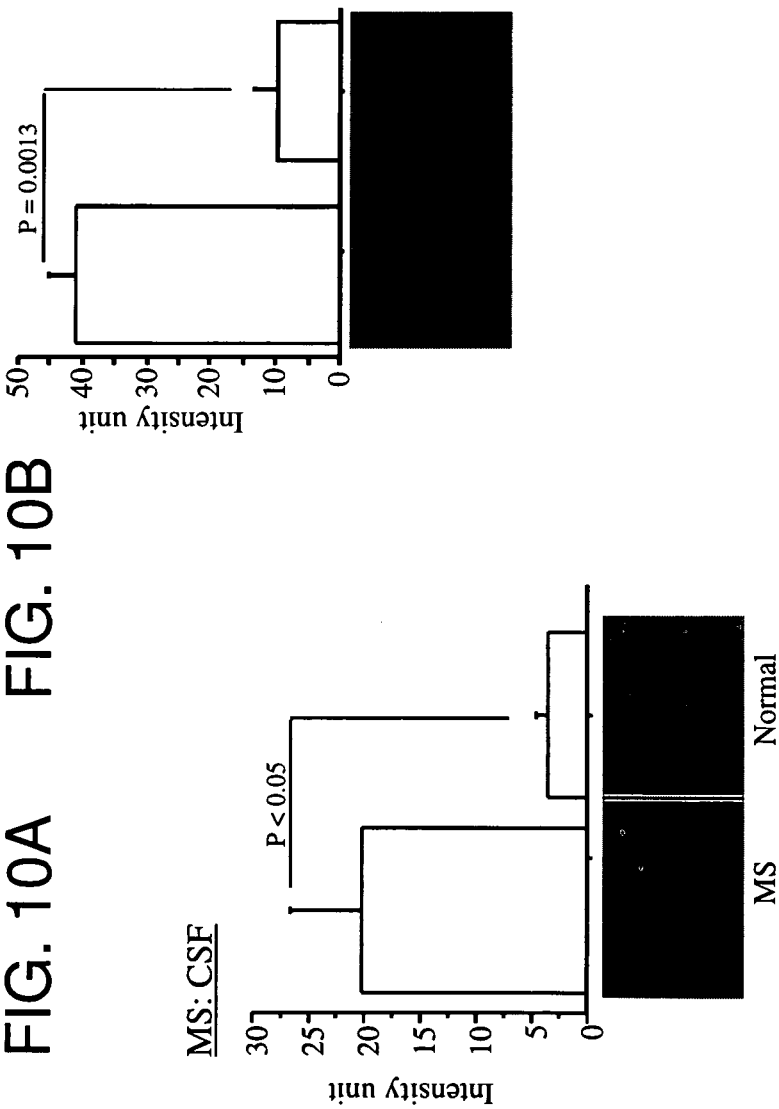

METHODS FOR TREATING AND PREVENTING MULTIPLE SCLEROSIS

CROSS-REFERENCE TO RELATED APPLICATIONS

The present application is a national phase application of PCT Application No. PCT/US2008/062158, filed on May 1, 2008, and claims priority to Provisional Appln. 60/915,127, filed May 1, 2007, the entire contents of which are hereby incorporated by reference as if fully set forth herein, under 35 U.S.C. §119(e).

STATEMENT OF GOVERNMENTAL INTEREST

This invention was made with Government support under US Public Health Service grant NO: NINDS 042855). The Government has certain rights in the invention.

BACKGROUND OF THE INVENTION

1. Field of the Invention

This invention is in the field of methods and pharmaceutical compositions for treating or preventing Multiple Sclerosis, Encephalitis, and other autoimmune diseases that are associated with an abnormal increase in the number of activated T-cells.

2. Description of the Related Art

Multiple sclerosis (MS) is a severe, chronic disabling disease that affects approximately 1 out of every 1,600 people. The majority of the affected individuals develop symptoms as young adults between 20 and 40 years of age, with roughly 60% of the cases occurring in women. The disease is characterized by neuron deterioration in the central nervous system (CNS) with the associated loss of the insulating myelin sheath from around the axons of the nerve cells, referred to as demyelination. The disease presents itself in the white matter of the brain and spinal cord as a number of sclerotic lesions or plaques (Prineas (1985) Demyelinating Diseases, Elsvevier: Amsterdam; Raine (1983) Multiple Sclerosis, Williams and Wilkins: Baltimore; Raine et al. (1988) J. Neuroimmunol. 20:189-201; and Martin (1997) J. Neural Transmission (Suppl) 49:53-67). The characteristic MS lesion is inflamed, exhibits axonal demyelination, axonal degeneration, and is found around small venules. These characteristics typically evolve early in plaque development and are hypothesized to occur as a result of a breakdown in the blood-brain barrier (BBB). As a consequence of BBB breakdown, infiltrates consisting of various lymphocytes and macrophages enter the brain or spinal cord. This inflammatory infiltrate ultimately leads to axonal degeneration and scar tissue formation, and in many instances, is associated with incomplete remyelination (Martin (1997) J. Neural Transmission (Suppl) 49:53-67). Further, it is hypothesized that this apparent immunologic attack targets not only the myelin sheath, but also the oligodendrocytes imperative to CNS myelin production. As a result, not only is the nerve-insulating myelin damaged, but the ability of oligodendroglial cells to repair damaged myelin is seriously compromised (Scientific American 269 (1993): 106-114). Development of multiple areas of scar tissue (sclerosis) along the covering of the nerve cells slows or blocks the transmission of nerve impulses in the affected area, resulting in the development of the symptoms characteristic of MS. These symptoms include pain and tingling in the arms and legs; localized and generalized numbness, muscle spasm and weakness; difficulty with balance when standing or walking; difficulty with speech and swallowing; cognitive deficits; fatigue; and bowel and bladder dysfunction.

Approximately half of the people with this disease suffer from relapsing-remitting MS. In these cases, the afflicted individual experiences repeated unpredictable attacks, due to episodes of inflammation, axonal demyelination, axonal degeneration, and development of glial scar tissue. These attacks are separated by periods of remission, during which the symptoms stabilize or diminish. Acute neurological deficits occur with each attack, and in many cases, the accumulation of residual deficits as a result of these attacks eventually leads to worsening disability and impairment in quality of life. Approximately 30-40% of the afflicted population have chronic progressive MS (either primary or secondary) in which neurological deterioration occurs in the absence of clinically apparent attacks. Recently, immunomodulatory therapy with interferon-beta (IFN-beta) has proven to be successful in reducing the severity of the underlying disease in patients with relapsing-remitting MS. FDA-approved IFN-beta therapies for the treatment of relapsing-remitting MS in the United States include interferon beta-1a (marketed as Avonex®, available from Biogen, Inc.) and interferon-beta-1b (marketed as Betaseron®, available from Chiron Corporation). Both of these therapeutic agents are partially effective in reducing the frequency and severity of relapses, slowing the rate of disease progression, or reducing the degree of brain inflammation as measured by a variety of magnetic resonance imaging (MRI) techniques.

MS is considered to be a T cell-mediated autoimmune disease of the brain and spinal cord [Traugott et al. 1983; Vizler et al. 1999]. The failed apoptosis of auto-reactive T cells has been implicated in MS pathogenesis. While there appears to be a localized CNS immune response, peripheral immune cell abnormalities appear to correlate with central disease activity [Hafler and Weiner 1989] and may precede MRI activity. Apoptosis is an important mechanism in immune system regulation, responsible for elimination of autoreactive T-lymphocytes (T cells), B-lymphocytes (B cells) and monocytes from the circulation and prevention of their entry into the CNS [Mahoney and Rosen 2005; Todaro et al. 2004]. It has been hypothesized that a genetic predisposition exists in MS patients whereby a failure of autoreactive T cells and B cells as well as activated macrophages to undergo apoptosis contributes to the pathogenesis of MS [Bernard and Derosbo 1992; Pender 1998; Pender and Rist 2001].

Prescribing decisions seem to be driven by evidence-based medicine and a recent report by the American Association of Neurologists (Goodin D S et al; Neurology Jan. 22, 2002; 58(2):169-78) is a key document. The consensus amongst many neurologists is that early, aggressive therapy with beta-interferons was desirable in increasing the time to first relapse and limiting the overall disease load, although it was recognized that there was no evidence that this approach showed long-term benefit on EDSS score (a measure of disease-related disability). There is currently no satisfactory diagnostic marker for multiple sclerosis. There is therefore a need for new diagnostic methods and for new disease-modifying therapies for MS.

SUMMARY OF THE INVENTION

A certain embodiment of the invention is directed to a method for treating or preventing multiple sclerosis (or another autoimmune disease) in a patient, by administering a therapeutically effective amount of an isolated anti-, antibody or biologically active fragment thereof. The isolated antibody can be the polyclonal anti-human LRG-47 antibody 138AB made in our laboratory and described herein, or a fragment or variant thereof, preferably a humanized form. Wherever a fragment of an antibody is mentioned herein it is understood that this fragment is a biologically active fragment or variant of the antibody. The antibody can also be a monoclonal, polyclonal, chimeric, humanized or bispecific anti-LRG-47 antibody or humanized antibody selected from the group comprising LRG-47 (A-19) Antibody, LRG-47 (M-95) Antibody, LRG-47 (M-16) Antibody, and LRG-47 (P-20) Antibody, anti-human LRG-47 138AB or fragment or variant thereof.

Another embodiment is directed to a method for treating or preventing multiple sclerosis (or another autoimmune disease) in a patient, by administering a therapeutically effective amount of a compound that decreases expression of human LRG-47. The compound can be an antisense nucleic acid or siRNA that is sufficiently complementary to the human gene or mRNA encoding LRG-47 to hybridize to it thereby forming a stable duplex.

Another embodiment is directed to a method for treating or preventing multiple sclerosis (or another autoimmune disease) in a patient, by a. determining a pre-treatment level of human LRG-47 protein in a pre-treatment biological sample taken from the animal, b. administering an amount of a compound that reduces human LRG-47 expression levels in animal cells (the above described siRNA or antisense nucleotide), c. determining a post-treatment level of human LRG-47 protein in a post-treatment biological sample taken from the animal, d. comparing the pre-treatment and post-treatment levels of LRG-47 protein in the respective biological samples, and e. determining that treatment is effective if the post-treatment level of LRG-47 is significantly lower than the pre-treatment level. This method optionally further includes the step f if the difference between the pre-treatment and post-treatment levels of LRG-47 are not significantly different, then increasing the amount or frequency of administration of the compound until the post-treatment level of LRG-47 is significantly lower than the pre-treatment level. A similar method can be used for an autoimmune disease.

A biological sample for the purpose of the present inventions can be a nerve sample, serum, blood, plasma, cerebral spinal fluid, fibroblasts, leukocytes, skin, or urine.

Another embodiment is directed to method for diagnosing a patient who is at risk of developing multiple sclerosis, by a. determining the level of human LRG-47 protein in a biological sample taken from the patient and in a corresponding sample taken from a control subject that is not affected with multiple sclerosis, b. comparing the level of LRG-47 protein in the biological samples and forming a diagnosis that the patient is at risk of developing multiple sclerosis if the level of LRG-47 protein in the patient sample is significantly higher than the level of LRG-47 protein in the control sample. A similar diagnostic method can be used to diagnose a patient at risk of developing an autoimmune disease. The method can have the further step of c. determining that the patient has multiple sclerosis if the patient shows other objective or subjective indicia of multiple sclerosis.

Another embodiment is directed to a method for determining the progression of multiple sclerosis, by a. determining the level of human LRG-47 protein in a first biological sample taken from the patient at a first time, b. determining the level of LRG-47 protein in a second biological sample taken from the patient at a second later time, c. comparing the level of LRG-47 protein in the first and second biological samples and diagnosing progression of multiple sclerosis if the level of LRG-47 protein in the second sample is significantly higher than the level of LRG-47 protein in the first sample. A similar method can be used to determine the progression of an autoimmune disease.

Another embodiment is directed to a method for determining if a patient is responding to treatment for MS, by a. determining the level of human LRG-47 protein in a first biological sample taken from the patient at a first time, b. determining the level of LRG-47 protein in a second biological sample taken from the patient at a second later time, c. comparing the level of LRG-47 protein in the first and second biological samples and determining that the patient is responding to treatment if the level of LRG-47 protein in the second sample is significantly lower than the level of LRG-47 protein in the first sample.

Another embodiment is directed to the new anti-human LRG-47 antibody 138AB and a fragment thereof, preferably a humanized form of the antibody, and to a pharmaceutical composition that includes the anti-human LRG-47 antibody 138AB or humanized fragment. Another embodiment is directed to a pharmaceutical composition that includes a humanized isolated anti-LRG-47 antibody or fragment thereof selected from the group including LRG-47 (A-19) Antibody, LRG-47 (M-95) Antibody, LRG-47 (M-16) Antibody, and LRG-47 (P-20) Antibody.

Another embodiment is directed to a diagnostic kit for determining the presence of human LRG-47 protein or human LRG-47 mRNA in a biological sample including: a) a) a vessel or vessels for receiving a blood, serum or CSF or cell sample from the subject; b) an agent that specifically detects LRG-47 protein or amplifies LRG-47 mRNA; and c) printed instructions for detecting the LRG-47 protein or the amplified LRG-47 mRNA in the sample. The agent that specifically detects LRG-47 protein can be an isolated anti-LRG-47 antibody selected from the group including LRG-47 (A-19) Antibody, LRG-47 (M-95) Antibody, LRG-47 (M-16) Antibody, LRG-47 (P-20) Antibody, and anti-human LRG-47 138AB Antibody, preferably humanized.

DESCRIPTION OF THE DRAWINGS

The present invention is illustrated by way of example, and not by way of limitation, in the figures of the accompanying drawings.

FIG. 1. Expression of LRG-47 in EAE mice (A-B). Total RNA was isolated from spinal cords of naïve, CFA (complete Freund's adjuvant)-treated and MBP-induced EAE mice. Quantitative real time PCR (A) shows transcripts of mouse LRG-47 in spinal cord tissues from each group on day 14 after induction of EAE (in the MBP-treated group; peak symptoms). * P<0.001, n=3-5 mice/group B. Northern analysis of spinal cord tissue for LRG-47 transcripts. Time points indicate days after immunization with MBP-derived peptide. C. Quantification of Northern blot images. * P<0.001, N=3/group. (D-E) Effect of gene deletion of LRG-47 on EAE. (D) LRG-47 hemizygous (LRG-47$^{+/-}$), homozygous (LRG-47$^{-/-}$) mice, and WT littermates (LRG-47$^{+/+}$) were immunized with 1-9NAc MBP-derived peptide. Symptoms were assessed according to a clinical scoring system (*P<0.01 vs. LRG$^{-/-}$ mice). (E). Lower panel, representative H & E-stained spinal cord sections from EAE-induced mice of the indicated genotype (LRG-47$^{+/+}$, LRG-47$^{+/-}$, and LRG-47$^{-/-}$) on day 21. Upper panel, analysis of area occupied by nuclei from samples derived from the above groups of mice (B-D). * P<0.01, n=3-4/group.

(F-I) Blockade of LRG-47 enhances apoptosis of encephalitogenic CD4$^+$ T-cells (1AE 10) in a dose- and time-dependent manner. (F) 1AE10 cells were activated with MBP (2.5 μg/ml) for 72 hours in the presence of anti-LRG-47 IgG (A-19, 0-20 μg/ml) or NI IgG (10 μg/ml). Apoptotic cells, as shown by annexin V staining, were assessed. #P<0.05, *P<0.01, n=3-5/group. Percentage of annexin V-positive cells (G), PI (propidium iodide)-positive cells (H), and live cells (I) were determined in the population of MBP-treated 1AE10 cells exposed to anti-LRG-47 IgG (A-19, 5 μg/ml) or NI IgG (5 μg/ml) for the indicated times. *P<0.01, n=3-5/group.

FIG. 4. Effect of blockade of LRG-47 on induction of EAE, apoptosis, and IFN-γ production. (A) Activated 1AE10 cells were adoptively transferred into appropriately prepared (see text) wild-type (WT) B10PL mice Animals received anti-LRG-47 IgG (blue), nonimmune IgG (green) or vehicle (black) as indicated. Clinical symptoms were scored. *P<0.01 vs. vehicle-treated or NI IgG-treated 1AE10 cells adoptively transferred into WT mice. (B) Apoptosis in the spinal cord of mice subject to adoptive transfer of activated 1AE10 cells. TUNEL-positive cells were quantified in spinal cords from WT mice after adoptive transfer of activated 1AE10 cells alone, transfer of 1AE10 cells and treatment with anti-LRG-47 IgG, or transfer of 1AE 10 cells and treatment with NI IgG. * P<0.01, n=3-5 mice/group. (C-E). Reduced accumulation and enhanced apoptosis of CD4 T-cells following adoptive transfer of 1AE10 cells into mice treated with anti-LRG-47 IgG. Mononuclear cells isolated from brain and spinal cord of mice subject to adoptive transfer of activated 1AE10 cells 16 and 28 days earlier were stained with anti-CD4-PE and annexin V-FITC followed by FACS analysis. FACS analyses show infiltrating CD4 T-cells (C, E) and annexin V-positive cells (D) in the CNS of the latter mice. FACS data shown in panels C-D (panels 1-3) are representative of 3-5 mice/group. Panels of C4, D4 and E4 display results of 3-4 experiments. Panels of D1-3 denote the percentage of apoptotic cells as shown by annexin V-positives in the right upper frame. (F-H). Blockade of LRG-47 increases IFN-γ production. (F) Levels of IFN-γ were determined in supernatants from cultured 1AE10 cells exposed to MBP in the presence of anit-LRG-47 IgG or NI IgG by ELISA. (G) Cytokine production in CD4 T-cells from WT and LRG-47$^{-/-}$ mice. CD4 T-cells were isolated from spleens of WT mice and LRG-47$^{-/-}$ mice, and cultured with MBP (2.5 μg/ml) for the indicated time. Levels of IFN-γ in culture supernatants were determined by ELISA. (H) Levels of IFN-γ in plasma from WT and LRG-47$^{-/-}$ mice immunized with MBP to develop EAE (day 14-18). * P<0.01, n=12-16 mice/group.

Figures 7B, 7C:
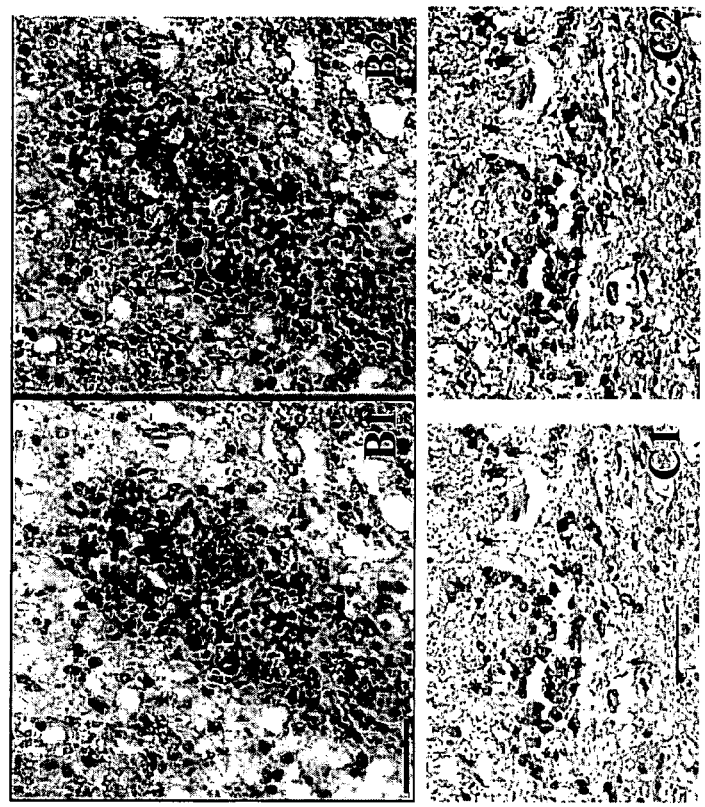

FIG. 5. SiRNA inhibition of LRG-47 expression in 1AE10 Cells. Panel 5a shows the level of LRG-47 mRNA in cells measured using RT-PCT. FIG. 7b shows the level of LRG-47 measured by Real-Time PCR. After stimulation with MBP (5 micrograms/ml) for 48 hours, 1AE10 T-cells were transfected with siRNA targeted to mouse LRG-47.

Figure 6:
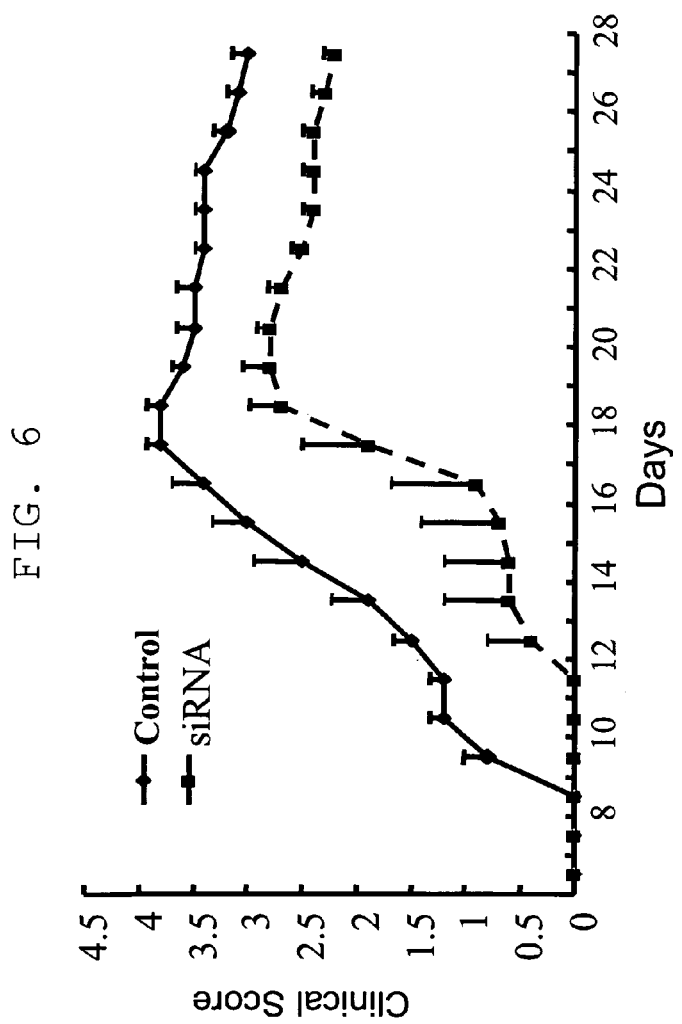

FIG. 6. Blockade of LRG-47 expression by siRNA attenuates the clinical symptoms in EAE mice. MBP-activated 1AE10 cells were treated with either siRNA-LRG 47 or vehicle, and adoptively transferred into B10PL mice. In wild-type (WT) B10PL mice treated with 1AE10 cells alone or 1AE10 cells, symptomatic EAE progressed rapidly, occurring in all animals in the 15-20 day window, and reaching a clinical score/severity of 3-4. In contrast, WT mice treated with 1AE10 cells exposed to siRNA-LRG 47 displayed a delay in the onset of EAE and attenuation of symptomatic EAE, a clinical score of only 1-2.5. Thus, clinical symptomatology mirrors what might be expected if LRG-47 was an essential cofactor for pathogenicity of 1AE10 cells.

FIG. 7 Expression of LRG-47 antigen in spinal cord tissue from MS patients. A. LRG-47 antigen was prominently elevated in MS-affected spinal cord tissue as compared with age-matched normal control by immunoblotting with specific anti-LRG-47 IgG. B-C. By immunostaining with specific anti-LRG 47 IgG, LRG-47 (B2 & C2) was especially present in mononuclear monocytes (B1) and CD4+ T cell (C1) as shown by co-stained with CD68 and CD4+, respectively (FIGS. 7B1 & C1. There was no positive staining when anti-LRG IgG was replaced by nonimmune IgG (data not shown). These data indicate the significance of LRG-47 in pathogenesis of MS and its relevance beyond EAE.

Figure 8:
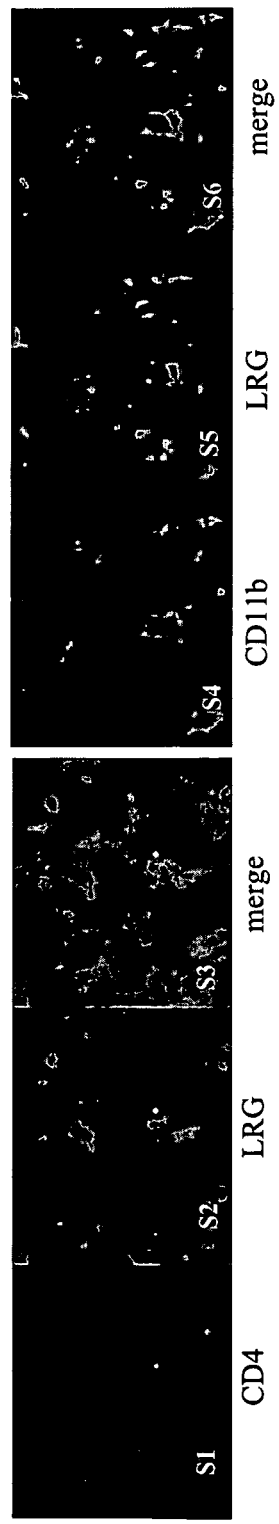

FIG. 8 Localization of LRG-47 antigen in spinal cords of EAE mice. Spinal cord sections were co-stained with goat anti-LRG-47 (1 micrograms/ml) and rat anti-CD4 or rat anti-CD11b followed by rabbit anti-goat IgG conjugated with FITC and anti-rat-conjugated with TRITC. LRG-47 antigen (panels S2 and S5) was detected in CD4+ T-cells (S1) and CD11b-positive mononuclear cells (S4). S3 and S6 are merged with S1/S2 and S3/S4, respectively. Magnification: S1-3, ×600; S4-6, ×400.

Figure 9:
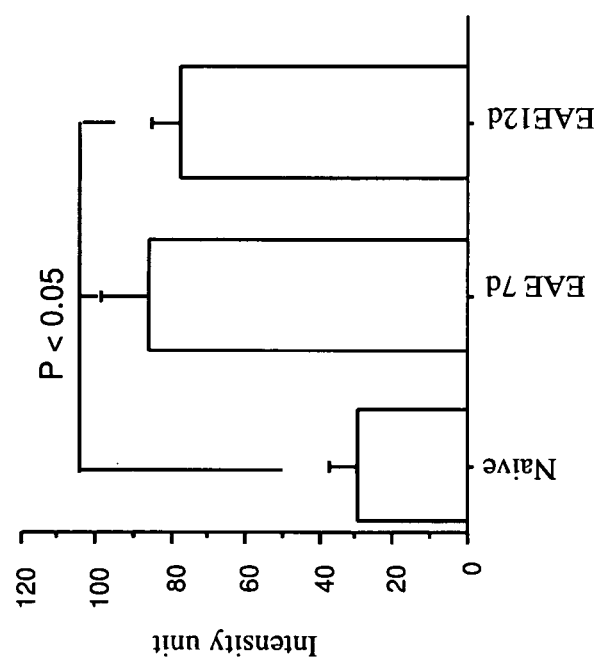

FIG. 9 Immuno-dot blotting with antibody to mouse LRG-47 of mouse serum from MBP-induced EAE mice at day 7 and 12 and naïve mice demonstrated an increase in LRG-47 in serum of EAE mice compared to serum from naïve mice. Levels of LRG-47 were quantified by NIH image program.

FIG. 10 Immuno-dot blotting with antibody to human LRG-47 of cerebral spinal fluid (CSF) and serum from MS patients demonstrated an increase in LRG-47 in MS patients compared to age-matched control patients. Levels of LRG-47 were quantified by NIH image program.

DETAILED DESCRIPTION

We have discovered that LRG-47 (also called p47 GTPase), plays a central role in the pathogenesis of multiple sclerosis, and that inhibition of LRG-47 activity by anti-LRG-47 antibodies or of LRG-47 expression by siRNA dramatically reduce the pathology and symptoms of multiple sclerosis. Therefore certain embodiments of the invention are directed to the therapeutic use of anti-LRG-47 antibodies (mouse or rabbit or other antibodies that are humanized or human antibodies to LRG-47, preferably antibodies made against human LRG-47) or siRNA or antisense nucleotides that specifically hybridize with the gene or mRNA or cDNA encoding human LRG-47 to treat or prevent multiple sclerosis and other autoimmune diseases that are T-cell-mediated. Other embodiments are directed to methods for the diagnosis of multiple sclerosis or to determining the aggressiveness of multiple sclerosis by determining the amount of human LRG-47 or LRG-47 mRNA in a biological sample from the patient. Other embodiments are directed to transgenic LRG-47−/− mice. Certain embodiments are directed to various humanized anti-LRG-47 antibodies and to their diagnostic and therapeutic use.

We have discovered that LRG-47 which is known for its essential contribution to host resistance to certain intracellular pathogens, plays a central role in the pathogenesis of Experimental Autoimmune Encephalitis (EAE) that is a model for Multiple Sclerosis in animals. The experiments herein show that LRG-47 increases the survival of autoreactive T-cells, the levels of which are known to be increased in animals having EAE. We show that expression of LRG-47 occurs early in the course of myelin basic protein (MBP)-induced EAE in the central nervous system (CNS), especially in cells of lymphoid and mononuclear phagocytic origin. Using classical genetics we discovered that homozygous LRG-47 null mice (hereafter "LRG-47 null mice") were resistant to MBP-induced EAE, and CD4 T-cells in the spleen and CNS of these animals displayed decreased proliferative capacity and underwent increased apoptosis. LRG-47 null mice also displayed dysregulation of interferon-γ. Certain embodiments of the invention are directed to LRG-47−/− transgenic mice.

The results of experiments presented below further show that an encephalitogenic CD4 Th1 clone (1AE10 cells) showed rapid upregulation of LRG-47 after exposure to MBP in vitro, while blockade of LRG-47 expression in the presence of MBP suppressed proliferation and induced cell death. Adoptive transfer of 1AE10 cells treated with anti-LRG IgG into naïve WT mice attenuated EAE when the mice were treated with MBP. These data indicate that one way in which the blockade of LRG-47 alleviates EAE is by suppressing expansion of activated CD4 T-cells. Importantly, we also discovered that LRG-47 expression levels are dramatically increased in spinal cord tissues taken from a patient diagnosed with Multiple Sclerosis (MS). The fluorescence detected by immunoblotting spinal cord tissue from an MS patient using an isolated antibody against LRG-47 was 16 times more intense than in normal animals. Further, we were able to block LRG-47 expression using small interfering RNA in 1AE10 cells in the EAE model and thereby reduce the severity of the disease and delay its onset.

These discoveries enable a therapy for treating or preventing MS by reducing the level of LRG-47 expression in an animal preferably a human that has the disease or is at risk of developing MS; preferably by reducing the level of expression in the central nervous system, more particularly in the spinal cord. Such inhibition can be accomplished by administering siRNA to an animal in an amount that either reduces LRG-47 expression in a biological sample taken from the animal, or in an amount that reduces the symptoms of MS in the animal. Since increased levels of activated CD4 T-cells are implicated in the pathogenesis of autoimmune disorders in general, certain embodiments of the invention are directed to methods of treating or preventing an autoimmune disorder in an animal preferably a human having elevated levels of activated CD4 T-cells by administering a therapeutic agent that reduces human LRG-47 expression.

Interferon-gamma (IFN-γ) plays a central role in host resistance to infection and regulation of the immune system. Thus, it is not surprising that INF-γ is an essential factor in CD4 T-cell homeostasis during the immune response, including activation-induced cell death [1-3]. In the setting of Experimental Autoimmune Encephalitis (EAE), INF-γ-deficient mice display a progressive and fatal clinical course associated with increased proliferation and decreased apoptosis of activated CD4 T-cells in response to antigen [3]. This pattern is also seen in other models of autoimmune diseases. These observations indicated to us the likelihood that downstream effectors of IFN-γ would also have important roles in immunobiology. Specifically, an IFN-γ-inducible family of intracellular 47 kDa GTPases has been shown to contribute to resistance to intracellular pathogens [4-9]. One member of this family, LRG-47, is essential in resistance to *Mycobacterial tuberculosis* and *Toxoplasma gondii*, whereas other members are involved in the response to different pathogens [4-9]. The results below demonstrate a role for LRG-47 in survival of autoreactive CD4 T-cells. In vivo and in vitro evidence shows that LRG-47 deficient mice show suppressed EAE because they do not show expansion of activated CD4 T-cells and decreased apoptosis of activated T cells.

We have recently demonstrated that receptor for advanced glycation endproducts (RAGE), a multiligand member of the immunoglobulin superfamily, can mediate induction of EAE under certain conditions. In the myelin basic protein (MBP) model used in the experiments described blow, blockade of RAGE prevents induction of symptomatic EAE, at least in part by inhibiting migration of immunocytes into the central nervous system [10]. In order to probe the underlying mechanisms, we performed microarray analysis to identify differences in gene expression between mice-induced by MBP and naïve mice. We discovered that LRG-47 was significantly upregulated in EAE-induced animals treated with MBP compared to naïve mice. The studies below that LRG-47 plays a key role in the pathogenesis of EAE and other autoimmune diseases associated with increased levels of activated T cells.

Results

Expression of LRG-47 in Mouse EAE

PCR demonstrated ≈30-fold upregulation of LRG-47 mRNA in spinal cord tissue in mice 14 days after treatment with MBP, when symptomatology was approaching a peak (15-17 days; see below), compared with controls (untreated animals or those receiving only complete Quantitative Freund's adjuvant, CFA; p<0.001)(FIG. 1A). Northern analysis on spinal cord from animals subjected to MBP-induced EAE was performed at several time points. A trend towards higher levels of LRG-47 transcripts was first noted on day 10 (post-MBP treatment), and a statistically significant increase was seen by day 14 (FIG. 1B-C) These data indicate a close correspondence between LRG-47 expression and symptomatic EAE. LRG-47 antigen was detected in CD4 T-cells (FIG. S1-3) and mononuclear phagocytes (FIG. S4-6) in spinal cords from EAE-induced mice by confocal microscopy. LRG-47 antigen was colocalized in a subpopulation of cells also staining for CD4 (FIG. S3) and CD11b (FIG. S6). These observations are consistent with a potential role of p47 GTPases in cells critical to the evolving host response.

Deficiency of LRG-47 Protects Animal from EAE

The close association of EAE with LRG-47 mRNA/protein expression led us to explore whether this mediator had a pathogenic role in EAE. To do this we used homozygous mutant mice devoid of LRG-47 (LRG-47$^{-/-}$) in the B10PL strain. For these studies, we employed the MPB model in which LRG-47$^{-/-}$ or age/strain-matched B10PL littermate mice were immunized with an acylated N-terminal peptide fragment comprised of nine residues from myelin basic protein (1-9NAc MBP)[10]. Compared to B10PL controls, LRG-47$^{-/-}$ mice exhibited strikingly reduced incidence and severity of disease (FIG. 1D, Table 1). Hemizygous LRG-47$^{+/-}$ mice showed a slight reduction in the severity of symptomatic disease compared with strain-matched wild-type (WT) littermates, though there was no significance between WT controls and LRG-47$^{+/-}$ mice (FIG. 1D). Histologic analysis of spinal cord tissue harvested at the time of peak symptoms (day 18) after treatment with MBP demonstrated a striking reduction in the inflammatory cell infiltrates in LRG-47$^{-/-}$ mice, compared with other genotypes (FIG. 1E). Thus, pathologic events correlate closely with symptomatology in terms of protection from disease in LRG-47$^{-/-}$ mice immunized with MBP.

TABLE 1

The percentage of each group of mice developing disease.

| Genotype | N | Incidence % |
|---|---|---|
| LRG+/+ | 12/12 | 100 |
| LRG+/− | 12/12 | 100 |
| LRG−/− | 2/12 | 16.7 |

Figure 2:
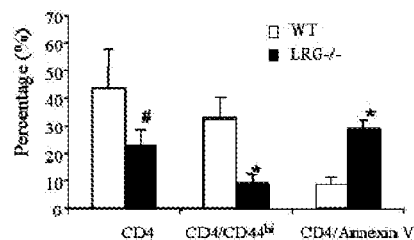
FIG. 2. LRG-47$^{-/-}$ mice display reduced accumulation and enhanced apoptosis of activated CD4 T-cells in the CNS during EAE (A-G). (A). Infiltrating cells were isolated from the CNS of LRG-47$^{-/-}$ mice and WT littermates on day 18-20 (peak symptomatic EAE, clinical score 3-4, in WT animals). Infiltrating cells isolated from the CNS were immunostained with antibodies to CD4 conjugated with PerCP, CD44 conjugated with PE, or Annexin V conjugated with FITC. FACS analyses were used to determine the percentage of cells staining positively for each of the markers, CD4, CD44$^{hi}$, and annexin V. CD44$^{hi}$ and annexin V were gated for CD4. * P<0.05, n=3-5/group. (B). FACS analysis of activated CD4 T-cells isolated from lymph nodes of mice induced to develop EAE with MBP. Lymphocytes isolated from lymph nodes of LRG$^{-/-}$ mice and WT littermates were stained with anti-CD4 conjugated with PerCP and CD44 conjugated with PE. The percentage of CD44$^{hi}$-positive cells was determined by FACS gated for CD4 cells. *P<0.01, n=3-5/group. (C). Lymphcytes in lymph nodes from EAE mice were subjected to TUNEL staining. TUNEL-positive cells were quantitated using UNIVERSAL image software. (D). In vivo proliferation of CD4$^+$ T-cells isolated from mice induced to develop EAE. Mononuclear cells isolated from the CNS were stained with anti-CD4 PerCP and anti-BrdU followed by FACS analysis. Cells were pooled from 5 mice of each group. BrdU incorporation was expressed as the percentage of BrdU-positive CD4$^+$ T-cells gated in CD4$^+$ T-cells. (E-G) Effect of LRG-47 gene deletion on T-cell proliferation and apoptosis of CD4 T-cells in response to MBP: in vitro studies. (E). $^3$H-thymidine incorporation was performed on lymphocytes and splenocytes isolated from the indicated mice on day 7 after immunization in the presence of MBP (2.5 μg/ml). * P<0.01 vs. other groups of mice, n=3-5/group. (F). Splenocytes from LRG-47$^{-/-}$ and WT littermates were stained with anti-CD4 conjugated to PE and annexin V conjugated to FITC after stimulation with MBP (2.5 μg/ml) for 48 and 72 hrs, respectively. FACS analyses show the percentage of annexin-positive cells gated in the CD4$^+$ T-cell population. (G). TUNEL-positive CD4 T-cells following exposure to MBP. CD4 T-cells isolated from spleens of LRG$^{-/-}$ and WT mice were incubated with MBP (2.5 μg/ml) for 48 hours and subjected to TUNEL staining. #P<0.05, *P<0.01, n=3-5/group.
Figure 2:
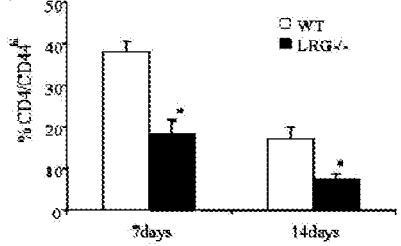
Figure 2:
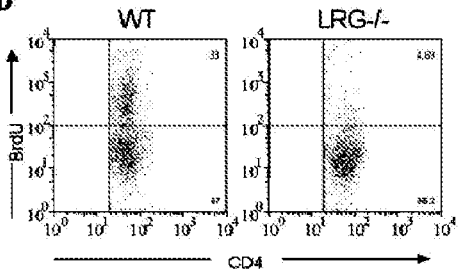
Figure 2:
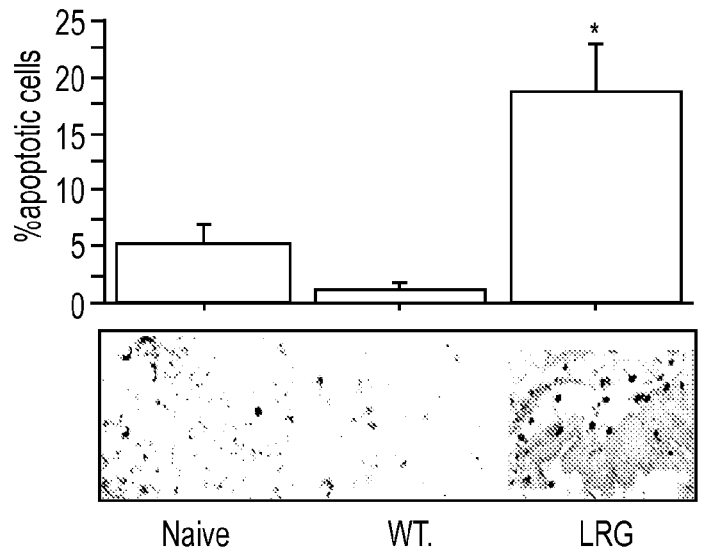

To begin to analyze mechanisms through which LRG-47 contributes to the pathogenesis of EAE, we analyzed the CD4 T-cell population in LRG-47$^{-/-}$ and control mice. The percentage of CD4 T-cells in the central nervous system (CNS), including brain and spinal cord eluates, from LRG-47$^{-/-}$ mice 20 days after MBP treatment was reduced ~50%, compared with strain-matched controls (22.7% and 46.6% for LRG-47$^{-/-}$ and controls, respectively)(FIG. 2A). The latter reduction was especially evident in the activated CD4 T-cell population that expresses high levels of CD44 (CD44$^{hi}$). Activated CD4 T-cells comprised only 8-9% of cells in spinal cord eluates from EAE-induced LRG-47$^{-/-}$ mice versus 32% in EAE-induced WT animals (FIG. 2A). Most striking was the ≈3-fold increase in apoptotic cells, based on annexin V staining, in the CD4 T-cell population harvested on day 20 from the CNS of LRG-47$^{-/-}$ mice compared with controls (30% versus 9%, for LRP-47$^{-/-}$ and controls, respectively; FIG. 2A). Similarly, the percentage of CD44$^{h1}$ activated CD4 T-cells was significantly reduced in the lymphocyte population from lymph nodes of LRG-47$^{-/-}$ mice compared to non-Tg (transgenic) littermate controls (FIG. 2B). A non-Tg littermate is an age-matched normal mouse in the same litters expressing endogenous levels of LRG-47 without transgene manipulation. Apoptosis of CD4 T cells, which includes activated T cells (shown as TUNEL-positive cells) was increased in the lymph nodes from LRG-47$^{-/-}$ mice, compared with WT littermates (FIG. 2C). To better understand the relationship between LRG-47 expression and cell proliferation in CD4 cells in vivo, mice received intraperitoneal BrdU, and FACS analysis was performed on cells isolated from the CNS using anti-CD4 and anti-BrdU IgG. Compared with WT littermate controls, cellular eluates from the CNS of LRG-47$^{-/-}$ mice displayed a strong reduction in the percentage of CD4 T-cells incorporating BrdU (4.69% in LRG-47$^{-/-}$ vs. 33% in WT mice; FIG. 2D). These data show a central role for LRG-47 in activation and/or expansion of autoreactive T-cells in EAE. Without being bound by theory, potentially, LRG-47 might promote survival of autoreactive T-cells in EAE.

Figure 2F:
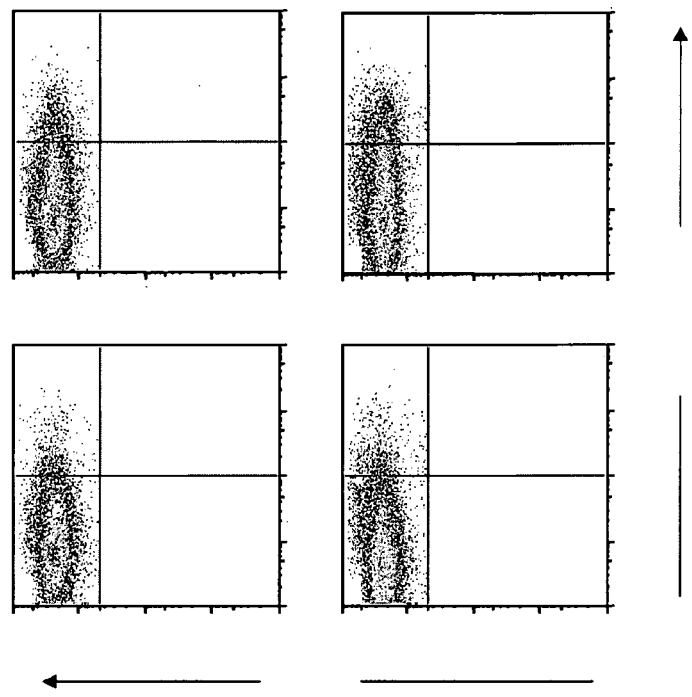
Figure 2E:
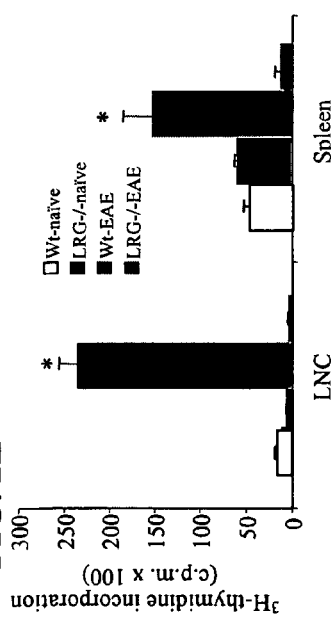
Figure 2G:
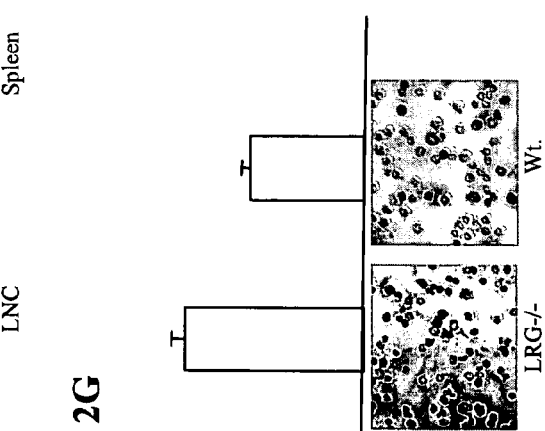

These in vivo observations concerning a possible relationship between LRG-47 expression and the proliferative potential of CD4 T-cells led us to perform in vitro experiments to directly address this issue. T-cells were purified from spleens and lymph nodes of mice immunized 7 days previously with MBP, and cultured in the presence of MBP. T-cells from LRG-47$^{-/-}$ mice showed diminished proliferation in response to MBP, compared with T-cells from WT littermate controls (FIG. 2E). Correspondingly, the percentage of annexin V-positive cells was increased in LRG-47$^{-/-}$ mice indicating increased apoptosis, versus WT (wild type) littermate controls (FIG. 2F). Further analysis of CD4 T-cells isolated from spleens of EAE mice after MBP treatment displayed an increase in the percentage of TUNEL-positive CD4 T-cells from LRG-47$^{-/-}$ mice compared with WT mice (FIG. 2G). These experiments provide further support the role of LRG-47 in activation of autoreactive T cells, and decreased apoptosis of autoreactive T cells during EAE.

Induction of EAE by Encephalitogenic T Cells: Effect of LRG-47

We next focused our experiments on an encephalitogenic CD4 Th1 T-cell clone (1AE10)[10] in order to assess the contribution of LRG-47 to EAE pathogenicity. Two approaches were utilized in these studies; 1) evaluation of the effect of LRG-47 on activation, proliferation and apoptosis of 1AE10 cells in vitro; and 2) determination of the impact of blocking LRG-47 activity on induction of EAE following adoptive transfer of activated 1AE10 cells in vivo. In order to characterize LRG-47 expression in 1AE10 cells, cultures were activated by addition of 1-9NAc MBP. LRG-47 transcripts increased by ~6-8-fold comparing day 0 to days 4-10 after stimulation with MBP (FIG. 3A). High levels of LRG-47 transcripts were maintained from days 4-10, and thereafter decreased. In view of heightened expression of LRG-47 in activated 1AE10 cells, we assessed whether inhibition of LRG-47 would modulate properties of 1AE10 cells.

LRG-47 mainly localizes to the Golgi apparatus [11, 12] as shown by colocalization with Golgi marker GRAS65. Unstimuated 1AE10 cells were stained with antibodies to LRG-47 (FIG. 5B2) or to GRAS65 (FIG. 5B1). LRG-47 was detected in Golgi apparatus (FIG. 3B3). However, after stimulation of 1AE10 cells with MBP (5 µg/ml) for 4 hours, LRG-47 translocated from Golgi to the plasma membrane of cell surface (FIG. 3C2-3) as shown on non-permeable cells. Therefore, LRG-47 appears to redistribute to the cell surface during activation of 1AE10 cells induced by MBP. These data led us to determine the effect of inhibiting LRG-47 on properties of 1AE10 cells using specific antibodies to LRG-47. The location of LRG-47 on the cell surface of the activated cells makes it accessible to antibodies for therapeutic intervention to reduce its effect.

Figure 3E:
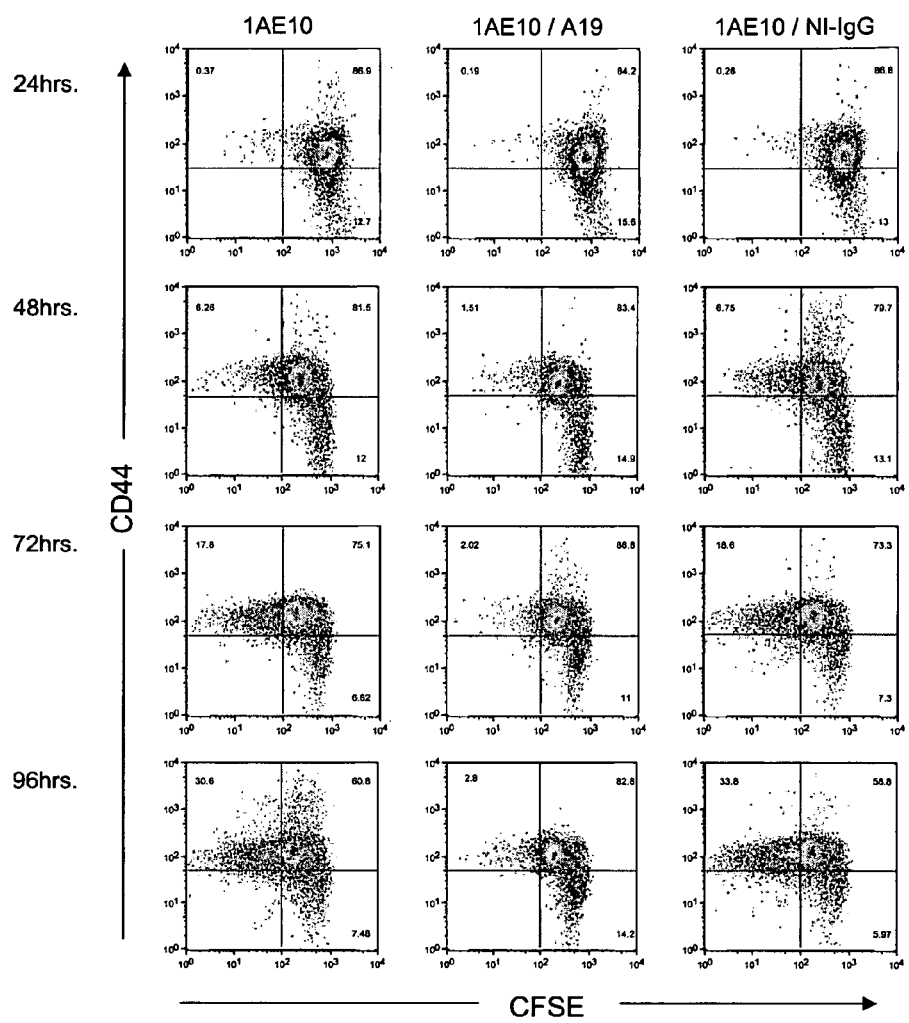
FIG. 3. Expression and translocation of LRG-47 in encephalitogenic CD4 T-cell (1AE10) and its effect on cell proliferation and apoptosis. (A) Northern blotting of 1AE10 cells shows elevated levels of LRG-47 transcripts in MBP-induced 1AE10 cells in a time-dependent manner (left panel). Image analysis of the intensity of bands is shown in the right panel. (B-C) Effect of MBP on LRG localization in 1AE10 cells. LRG-47 was localized in the Golgi compartment of unstimulated 1AE10 cells (panel B). When 1AE10 cells were stimulated with MBP (5 μg/ml) for 4 hours, LRG-47 was redistributed from Golgi apparatus to the cell membrane (panels C1-C3). B1 & C1:GSK65 (marker for Golgi) staining; B2 & C2: LRG-47 staining; B3 & C3 merge images from B1/B2 and C1/C2, respectively. Addition of anti-LRG-47 IgG attenuates $^3$H-thymidine incorporation (D) and proliferation (E) in MBP-treated 1AE 10 cells. (E) CFES-labeled 1AE10 cells were stimulated by the presence of MBP (2.5 μg/ml) for the indicated times (24 to 96 hours) and stained by anti-CD44 conjugated to PE. The CFSE fluorescence profile was analyzed by FACS gated for CD44+ T-cells.

Activation of 1AE10 cells for 4 days in culture with MBP resulted in a corresponding increase in $^3$H-thymidine incorporation which was blocked in a dose-dependent manner by anti-LRG-47 IgG (A-19), but not by nonimmune (NI) IgG (FIG. 3D). Consistent with these data, FACS analysis of CFSE-FITC-labeled 1AE10 cells activated by exposure to MBP displayed time-dependent proliferation; cell labeling increased from 0.37% to 30.6% corresponding to the interval from 24 hour to 96 hours. The latter proliferative response was inhibited by ~10-fold at the 96 hour time point on addition of anti-LRG-47 IgG (A19). In contrast, NI IgG had no effect (FIG. 3E). These data indicate that blockade of LRG-47 suppresses antigen induced proliferation of encephalitogenic T-cells.

Apoptosis of lymphocytes is one of the major homeostatic mechanisms in the immune system. In view of the enhanced susceptibility of LRG-47$^{-/-}$ mice to protozoan and mycobaterial infection [7, 13, 14], we sought to determine whether LRG-47 functioned as a survival factor in MBP-primed encephalitogenic T-cells. To address this issue, we examined if the lack of proliferative activity in 1AE10 cells activated in the presence of MBP actually reflected an enhanced degree of apoptosis. MBP-treated 1AE10 cells displayed a dose-dependent increase in the population of annexin V-positive cells as the concentration of anti-LRG-47 IgG was increased from 5 to 20 µg/ml reaching up to ≈70% of the cells, whereas NI IgG was without effect (72 hr time point; FIG. 3F). These results were paralleled by those observed on time-dependent assessment of annexin V staining (FIG. 3G), propidium iodide uptake (FIG. 3H), and live cell assay (FIG. 3I) in 1AE10 cells. Addition of anti-LRG-47 IgG showed evidence of increased cell death/apoptosis in each case. These data show that LRG-47 is a key factor in expansion of encephalitogenic CD4 T-cells in response to antigen, in this case MBP, by inhibiting apoptosis.

Figure 4D:
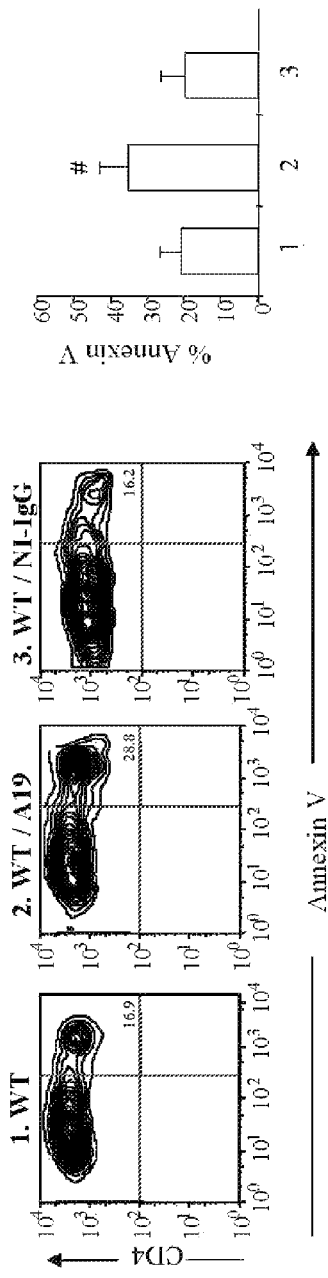

The ultimate confirmation of this result concerns the encephalitogenic potential of 1AE10 cells in vivo. MBP-activated 1AE10 cells were treated with either anti-LRG-47 IgG or NI IgG, and adoptively transferred into B10PL mice. Wild-type (WT) B10PL mice treated with 1AE10 cells alone or with 1AE10 cells/NI IgG, showed symptomatic EAE that progressed rapidly, occurring in all animals in the 12-14 day window, and reaching a clinical score/severity of 3-4 (FIG. 4A, Table 2). In contrast, WT mice treated with 1AE10 cells exposed to anti-LRG-47 IgG (A-19) displayed only 77.8% incidence of symptomatic EAE, with a quite different course (delayed) and a dramatically lower clinical score of only 1-1.5. Thus, clinical symptomatology mirrors what is expected if LRG-47 was an essential cofactor for pathogenicity of 1AE10 cells.

TABLE 2

| Transfer EAE | N | Incidence % |
|---|---|---|
| WT. | 9/9 | 100 |
| Wt./A19 | 7/9 | 77.8 |
| Wt./NI-IgG | 6/6 | 100 |

Figure 4E:
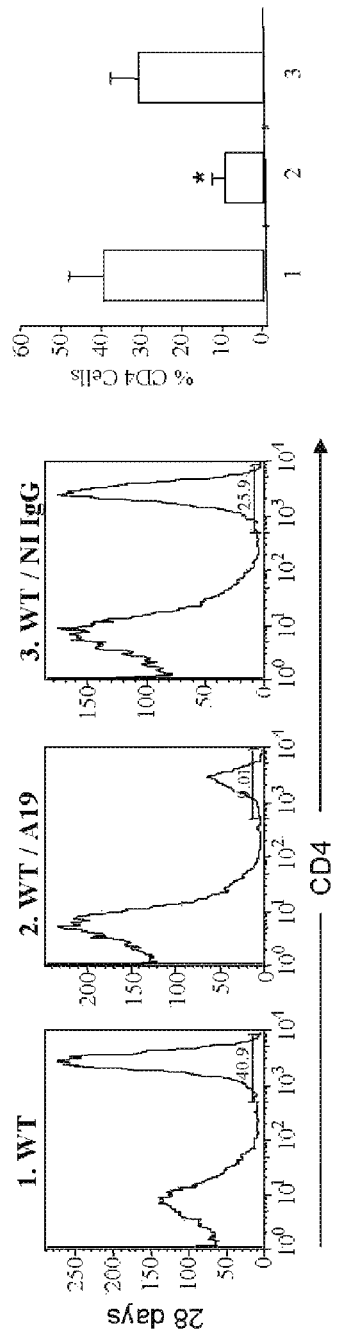

Our clinical findings in mice indicated the importance of analyzing the nature of cells infiltrating the spinal cord under each of these situations following induction of EAE by infusion of 1AE10 cells. At day 14-16, during the peak of EAE symptoms, there were no significant differences in the number of CD4 T-cells in spinal cord eluates among WT mice adoptively transferred with 1AE10 cells that were treated with anti-LRG-47 IgG, control NI IgG, or in 1AE10 cells alone without any treatment. (FIG. 4C). However, apoptotic cells in spinal cord eluates, as shown by annexin V and TUNEL staining, showed substantial differences in each of these situations. Whereas there were fewer apoptotic cells in eluates from WT mice transferred with 1AE10 cells alone or treated with control NI IgG, there were significantly more apoptotic cells in samples from WT mice transferred with 1AE10 cells treated with anti-LRG-47 IgG (A19)(FIG. 4B, D). Thus, death of CD4 T-cells in the spinal cord between days 14 and 28, was the likely explanation for their reduction in spinal cord eluates in WT mice transferred with 1AE10 cells treated with anti-LRG-47 IgG, versus WT mice treated with 1AE10 cells alone observed at days 28 (FIG. 4E).

Effect of LRG-47 on IFN-γ Induction

Figure 4F:
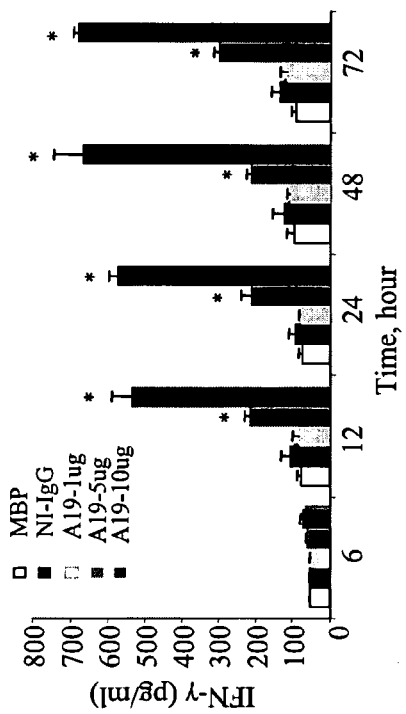
Figure 4H:
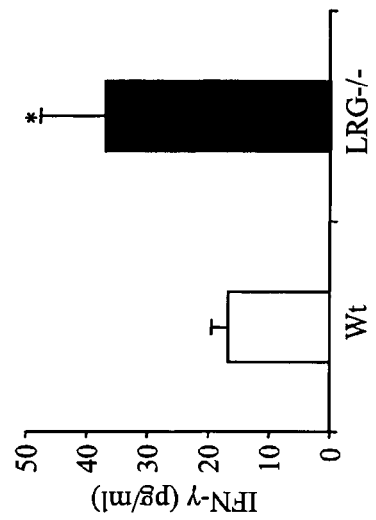
Figure 4G:
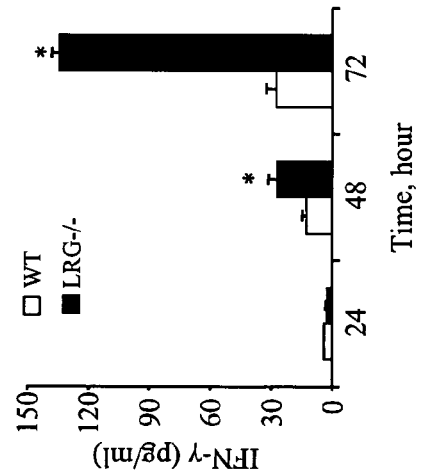

To further understand the role of LRG-47 in regulating CD4 T-cell function/survival in the setting of pathogenic auto-immunity, we examined how LRG-47 expression affects the expression of IFN-γ in 1AE10 cells. Cultured 1AE10 cells were stimulated with MBP-derived peptide alone or with MBP-derived peptide in the presence of either anti-LRG-47 IgG or NI IgG. IFN-γ was measured in supernatants (FIG. 4F). We found that LRG-47 is a negative regulator of IFN-γ. Inhibition of LRG-47 in cultured 1AE10 cells with anti-LRG-47 IgG resulted in dose- and time-dependent increases in levels of IFN-γ (FIG. 4F) secreted into the medium. Moreover, IFN-γ levels were increased in cultured CD4 T-cells isolated from lymph nodes/spleens of LRG-47$^{-/-}$ mice at 7 days after immunization with MBP-derived peptide (FIG. 4G). In addition, levels of IFN-γ were elevated in the sera of LRG-47$^{-/-}$ mice compared to WT mice induced with MBP to develop EAE (FIG. 4H).

Multiple sclerosis is the most common autoimmune disease of the central nerve system (CNS). T lymphocytes that are reactive with components of myelin sheaths are thought to play key roles in disease pathogenesis. Experimental autoimmune encephalitis (EAE) is the best animal model of multiple sclerosis. During EAE, the interaction of active CD4+ T cells and myelin antigens apparently provoke a massive destructive inflammatory response that promotes continuing proliferation of T cells and macrophage activation that escalates to intensive inflammation and dymyelination of nerves in the CNS. The presence of LRG-47 in auto-reactive CD4+ T cells and macrophages, and increased expression of LRG-47 in EAE-affected spinal cord tissue indicate a key role of LRG-47 on the induction of EAE. Blockade of LRG-47 expression promotes apoptosis, which diminishes expansion of activation and proliferation of MBP-reactive CD4+ T cells. Furthermore, activation of an encephalitogenic CD4+ Th1 T-cell clone with MBP was clearly suppressed in the presence of anti-LRG-47 specific IgG but not by non-immune IgG. At the same time, apoptotic cells were significantly increased in response to LRG-47 blockade. Also, LRG-47 blockade prevented induction of EAE when fully activated 1AE10 cells were transferred into B10.PL mice. Blockade of LRG-47 also increased apoptotic encephalitogenic CD4+ T cells in EAE-affected spinal cord tissues. These data show a requirement of LRG-47 protein for persistence of CD4 T-cells in the CNS to propagate the immune/inflammatory response. Thus it is likely that death of encephalitogenic CD4 T-cells and their decreased proliferation account for the relatively mild course of EAE in WT animals adoptively transferred with 1AE10 cells treated with anti-LRG-47.

IFN-γ has been shown to function as a negative regulator of lymphocyte expansion, eliminating activated CD4 T-cells by promoting apoptosis during the immune response [1-3, 17]. Without being bound by theory, we propose that blockade of LRG-47 interrupts a negative feedback loop that is triggered after the immune response is initiated, thereby limiting subsequent expression of IFN-γ. As a result, re-expression of IFN-γ leads to levels which attenuate the ongoing immune response.

While LRG-47 has been shown to contribute to the host response to intracellular bacterial infection [9, 12, 16] and has been suggested to function as a survival factor in the context of mycobacterial infection [14, 18]. Our data indicate that it is also present in CD4 T-cells where it promotes survival of pathogenic self-reactive T-cells at least in part by preventing T-cell apoptosis. Without being bound by theory, we propose that induction of EAE by activation of autoreactive MBP-specific T-cells leads to early (day 7) secretion of IFN-γ initiating a DTH (Delayed Type Hypersensitivity) response in the CNS. Induction of LRG-47 by IFN-γ facilitates the survival of the expanded self-reactive T-cell population, thus LRG-47 also plays an important role in the pathogenesis of autoimmune disease including MS and EAE. This protective role of LRG-47 for encephalitogenic CD4 T-cells in EAE (thereby enhancing their pathogenicity) contrasts with its role in buttressing a protective host response to certain pathogens [4, 7, 12, 14]. The translocation of LRG-47 to the outer cell membrane adds a new and unexpected dimension to the biology of this GTPase. Its location on the outer cell membrane means that it is an accessible target for immune therapy (i.e. blocking LRG-47 activity with anti-LRG-47 antibodies.) Certain embodiments of the invention are directed to treating or preventing an autoimmune disease including MS by administering anti-LRG47 antibodies or fragments or variants thereof, preferably in humanized form and preferably against human LRG-47, in order to reduce LRG-47 expression.

SiRNA Effectively Blocks LRG-47 Expression in 1AE10 T-Cells

To test the ability of SiRNA to block LRG-47 expression, 1AE10 T-cells were stimulated with MBP (5 micrograms per ml) for 48 hours. 1AE10 T cells were transfected with siRNA targeted to mouse LRG-47 (sense sequence: 5'-GGUUAC-CUGAGGUCAGUAGtt-3' SEQ ID NO: 5, antisense sequence: 5'-CUACUGACCUCAGGUAACCtg-3' SEQ ID NO: 6) using siPORT Amine (Ambion) for additional 24. Levels of LRG-47 mRNA in cells were determined by real-time quantitative PCR and RT-PCR. The level of LRG-47 mRNA was measured using real-time quantitative PCR (right) and RT-PCR (left). The results shown in FIG. 5 show that LRG-47 expression was reduced by about 40% by transfection with the siRNA. In addition to reviewing the level of LRG-47 mRNA expression, we also looked at the clinical symptoms in EAE in vivo. Blockade of LRG-47 expression by siRNA attenuates the clinical symptoms in EAE mice. MBP-activated 1AE10 cells were treated with either siRNA-LRG 47 or vehicle, and adoptively transferred into B10PL mice. In wild-type (WT) B10PL mice treated with 1AE10 cells alone or 1AE10 cells, symptomatic EAE progressed rapidly, occurring in all patients in the 15-20 day window, and reaching a clinical score/severity of 3-4. In contrast, WT mice treated with 1AE10 cells exposed to siRNA-LRG 47 displayed a delay in the onset of EAE and attenuation of symptomatic EAE, a clinical score of only 1-2.5. Thus, clinical symptomatology mirrors what might be expected if LRG-47 was an essential cofactor for pathogenicity of 1AE10 cells.

As is discussed below certain embodiments of the invention are directed to methods for treating or preventing MS by administering an agent that reduces LRG-47 expression, preferably human LRG-47 for human use, including siRNAs. Although we tested only one siRNA against a murine LRG-47, the field of antisense technology is well established and it is routine in the art to develop antisense or siRNA molecules that inhibit expression of a given target gene or mRNA.

LRG-47 Levels are Elevated about Spinal Cord, CSF and Serum from MS Patients

Figure 7A:
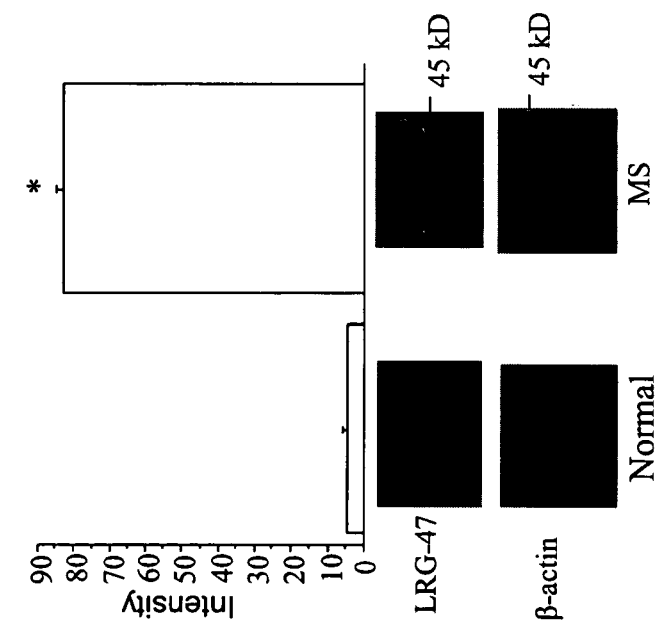

In order to determine whether LRG-47 levels are elevated in a human patient having MS, we analyzed MS-affected spinal cord tissues. LRG-47 levels were measured using quantitative real-time PCR, which showed an approximately 16-fold increase in LRG-47 in the MS-affected patient sample, compared to a spinal cord sample from an age-matched unafflicted control. FIG. 7 shows expression of LRG-47 antigen in spinal cord tissue from MS patients. FIG. 7A. LRG-47 antigen was prominently elevated in MS-affected spinal cord tissue as compared with age-matched normal control by immunoblotting with specific anti-LRG-47 IgG. FIG. 7B-C Immunostaining with specific anti-LRG 47 IgG, showed that LRG-47 (B2 & C2) was especially intense in mononuclear monocytes (B1) and CD4+ T cell (C1), as shown by co-staining with CD68 and CD4+, respectively (FIGS. 7B1 & C1). There was no positive staining when anti-LRG IgG was replaced by nonimmune IgG (data not shown). These results taken together show the significance of LRG-47 expression in the pathogenesis of MS and its relevance to autoimmune diseases other than EAE.

FIG. 8 shows the localization of LRG-47 antigen in spinal cords of EAE mice. Spinal cord sections were co-stained with goat anti-LRG-47 (1 micrograms/ml) and rat anti-CD4 or rat anti-CD11b, followed by rabbit anti-goat IgG conjugated with FITC, and anti-rat-conjugated with TRITC. LRG-47 antigen (panels S2 and S5) was detected in CD4+ T-cells (S1) and CD11b-positive mononuclear cells (S4). S3 and S6 are merged with S1/S2 and S3/S4, respectively. Magnification: S1-3, ×600; S4-6, ×400.

Recently, we showed that level of LRG-47 was increased in the serum of EAE mice compared to the serum of naïve mice. Similarly, LRG-47 was up-regulated in the cerebral spinal fluid (CSF) or serum taken from MS patients at the activated stage. FIG. 9 shows immuno-dot blotting with antibody to mouse LRG-47 of mouse serum demonstrating a significant increase in LRG-47 in the serum of EAE mice compared to serum from naïve mice. Levels of LRG-47 were quantified by NIH image program. Naïve mice showed about 25 units of intensity compared to about 85 for EAE mice at day 7 and about 80 for day 12, indicating more than a 3-fold increase in serum LRG-47. We next looked at human CSF and serum from MS patients compared to age-matched control patients using the to anti-human-LRG-47 AB antibody that was made in our laboratory. The results an approximate 4-fold increase in the levels of LRG-47 in the serum and CSF of MS patients. Based on these results we describe diagnostic methods below based on measuring elevated levels of secreted LRG-47 in serum or CSF of a patient compared to controls. Certain embodiments are also directed to the new anti-human-LRG-47 138AB antibody itself, or fragments or variants thereof, preferably in humanized form. Embodiments are also directed to pharmaceutical formulations comprising the new anti-human-LRG-47 138AB antibody itself, or fragments or variants thereof, preferably in humanized form; and to its use to treat, prevent or diagnose MS or other autoimmune disease.

We made rabbit anti human LRG-47 antibody, called 138AB as follows: Synthetic peptides [Ac-VGHEGKASPPTELVKATQR-amide (54-71) SEQ ID NO: 7 and Ac-EDMGKKFYIVWTKLDMDLC-amide (132-149))] SEQ ID NO: 8 were immunized to rabbit, and then antiserum was affinity purified to IgG. This affinity purified antibody specific for human LRG was used for our study. Certain embodiments are directed to this antibody or a fragment or variant thereof preferably in humanized form, and to its therapeutic use to treat, prevent or diagnose MS or other autoimmune disease.

Treatment and Prevention of MS Using Anti-LRG-47 Antibodies

Certain embodiments of the invention are directed to methods to treat or prevent MS in an animal, preferably a human, by administering a therapeutically effective amount of an isolated anti-LRG-47 antibody or biologically active fragment thereof, including polyclonal and monoclonal antibodies preferably humanized. In a preferred embodiment the isolated antibody is a polyclonal anti-human LRG47 antibody named 138AB or fragment or variant thereof that was made in our laboratory as described herein. An embodiment of the invention is also directed to this isolated polyclonal anti-human LRG47 138AB or fragment or variant thereof, preferably a humanized form, and to its therapeutic use as described herein. In another preferred embodiment the isolated antibody for use in treating or preventing MS includes humanized forms of the polyclonal anti-LRG47 antibodies commercially available from Santa Cruz Biotechnology, Inc. including those listed below, or a fragment or variant thereof. These antibodies can also be used to measure the level of secreted LRG-47 in a biological sample as described herein for diagnostic testing, and can be included in the kits described below. Non humanized forms can be used for the diagnostic claims herein.

For the purpose of this invention, a therapeutically effective amount of a compound is an amount that achieves the desired biologic or therapeutic effect, namely an amount that prevents, reduces or ameliorates one or more symptoms of the enumerated diseases being treated or prevented. In some embodiments the starting point for determining a therapeutic amount is an amount that significantly reduces the amount of secreted LRG-47 protein or LRG-47 mRNA in a patient biological sample, (i.e. a statistically significant reduction, preferably a two fold reduction).

The location of LRG-47 protein on the surface of activated T cells is particularly important for treating or preventing MS using antibody therapy because this target protein is accessible to the antibodies. Anti-LRG-47 therapy targets circulating activated T cells, so the antibody does not need to cross the BBB. The amount of anti-LRG-47 to be administered therapeutically ranges from about 1 ug to 100 ug/ml. This amount typically varies and can be an amount sufficient to achieve serum therapeutic agent levels typically of between about 1 microgram per milliliter and about 10 micrograms per milliliter in the subject. In the context of the present invention, anti-LRG-47 antibodies are a type of neutralizing antibody that prevents LRG-47 from activating T cells.

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab').sub.2, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50 70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as .kappa. and .lamda. light chains. Heavy chains are classified as .mu., .DELTA., .gamma., .alpha., or .epsilon., and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of

| PRODUCT NAME | CATALOG # | ISOTYPE | EPITOPE | APPLICATIONS |
| --- | --- | --- | --- | --- |
| LRG-47 (M-95) Antibody | sc-33216 | rabbit IgG | 315-409 (m) | WB, IP, IF, ELISA |
| LRG-47 (P-20) Antibody | sc-11074 | goat IgG | N-terminus (m) | WB, IF, ELISA |
| LRG-47 (M-16) Antibody | sc-11077 | goat IgG | C-terminus (m) | WB, IF, ELISA |
| LRG-47 (A-19) Antibody | sc-11075 | goat IgG | N-terminus (m) | WB, IF, ELISA |

LRG-47 specific siRNA gene silencers are also available. These include: LRG-47 siRNA (m): sc-41794.

amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901 917 (1987); Chothia et al. Nature 342:878 883 (1989).

An Fab fragment is a monovalent fragment consisting of the VL, VH, CL and CH I domains; a F(ab').sub.2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544 546, 1989) consists of a VH domain.

A single-chain antibody (scFv) is an antibody in which a VL and VH regions are paired to form a monovalent molecules via a synthetic linker that enables them to be made as a single protein chain (Bird et al., Science 242:423 426, 1988 and Huston et al., Proc. Natl. Acad. Sci. USA 85:5879 5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444 6448, 1993, and Poljak, R. J., et al., Structure 2:1121 1123, 1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293, incorporated herein by reference.

The term "chimeric antibody" refers to an antibody that contains one or more regions from one antibody and one or more regions from one or more other antibodies.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

Antisense Nucleotides and siRNA

Certain embodiments of the invention are directed to the use of antisense or siRNA to block expression of LRG-47 thereby treating or preventing MS or other autoimmune or T-cell mediated diseases, preferably in humans. Antisense nucleotides can be designed using routine skill in the art to target human DNA or mRNA encoding LRG-47 as is described in more detail below. The full cDNA sequence for the human LRG-47 gene is not yet known; the partial sequence known at the present time is public and is set forth in BC128168, incorporated herein by reference as SEQ ID NO: 1. When the full sequence becomes known and published, persons of skill in the art will be able to construct appropriate antisense nucleotides and siRNA using methods known in the art. The gene and mRNA sequence for mouse LRG-47 is public, is identified by accession NO: U19119, and is incorporated herein by reference as SEQ ID. No:3 (gene sequence) and SEQ ID NO: 4 (amino acid sequence).

Another embodiment for treating or preventing multiple sclerosis in an animal preferably a human, has the steps:

a. determining a pre-treatment level of human LRG-47 protein in a pre-treatment biological sample taken from the animal, b. administering an amount of an antisense nucleotide or siRNA that specifically hybridizes with the gene or mRNA encoding LRG-47, c. determining a post-treatment level of LRG-47 protein in a post-treatment biological sample taken from the animal, d. comparing the pre-treatment and post-treatment levels of LRG-47 protein in the respective biological samples, and e. determining that treatment is effective if the post-treatment level of LRG-47 is significantly lower than the pre-treatment level.

The method includes further step f if the treatment is not effective: if the difference between the pre-treatment and post-treatment levels of LRG-47 protein is not significantly different, then increasing the amount or frequency of administration of the antisense or siRNA until the post-treatment level of LRG-47 is significantly lower than the pre-treatment level. These same basic methods can be used to treat any autoimmune disease because all are associated with elevated levels of activated T cells.

Any compound that inhibits LRG-47 expression can be used to treat or prevent MS or an autoimmune disease.

Any method known in the art for measuring LRG-47 expression (measuring LRG-47 protein levels or mRNA, including using PCR and Northern blot hybridization) in the biological sample can be used including those described herein. By "significantly lower" is meant that there is a statistically significant difference between pre- and post-treatment levels of LRG-47 protein or mRNA. LRG-47 can be measured in any biological sample, preferably serum or cerebrospinal fluid (CSF), or blood using any method known in the art. Biopsy samples (for example of skin and fibroblasts), if available, can also be analyzed. The siRNA or antisense compounds directed to LRG-47 DNA or mRNA can be formulated into a pharmaceutical carrier using any method known in the art, and administered by any method known in the art.

The isolated antisense or siRNA nucleic acid molecules for use in the invention comprise a nucleic acid molecule which is a complement of the partial cDNA (confirm it is cDNA) sequence shown in SEQ ID NO:1, encoding human LRG-47, or a portion thereof. Antisense can also be complementary to mRNA encoding LRG-47. A nucleic acid molecule which is complementary to a given nucleotide sequence is one which is sufficiently complementary to the given nucleotide sequence that it can hybridize to the given nucleotide sequence thereby forming a stable duplex.

Antisense nucleic acid molecules, i.e., molecules which are complementary to a sense nucleic acid encoding a protein, e.g., complementary to the coding strand of a double-stranded DNA molecule (or cDNA) or complementary to an mRNA sequence. Accordingly, an antisense nucleic acid can hydrogen bond to a sense nucleic acid. The antisense nucleic acid can be complementary to an entire LRG-47 coding strand, or to only a portion thereof, e.g., all or part of the protein coding region (or open reading frame). An antisense nucleic acid molecule can be antisense to a noncoding region of the coding strand of a nucleotide sequence encoding LRG-47. The noncoding regions ("5' and 3' untranslated regions") are the 5' and 3' sequences which flank the coding region and are not translated into amino acids.

Given the coding strand sequences encoding LRG-47 disclosed herein (e.g., SEQ ID NO:1), antisense nucleic acids of the invention can be designed according to the rules of Watson and Crick base pairing. The antisense nucleic acid molecule can be complementary to the entire coding region of LRG-47 mRNA, but more preferably is an oligonucleotide which is antisense to only a portion of the coding or noncoding region of LRG-47 mRNA. For example, the antisense oligonucleotide can be complementary to the region surrounding the translation start site of LRG-47mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-hodouracil, hypoxanthine, xanthine, 4-acetylcytosine, 5-(carboxyhydroxylmethyl) uracil, 5-carboxymethylaminomethyl-2-thouridine, 5-carboxymethylaminometh-yluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-cxyacetic acid (v), 5-methyl-2-thiouracil, 3-(3- amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding the protein of interest to thereby inhibit expression of the protein, e.g., by inhibiting transcription and/or translation. The hybridization can be by conventional nucleotide complementary to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an alpha-anomeric nucleic acid molecule. An .alpha.-anomeric nucleic acid molecule forms specific double-stranded hybrids with complementary RNA in which, contrary to the usual .beta.-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330). All of the methods described in the above articles regarding antisense technology are incorporated herein by reference.

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave LRG-47mRNA transcripts thereby inhibit translation of LRG-47mRNA. A ribozyme having specificity for an LRG-47-encoding nucleic acid can be designed based upon the nucleotide sequence of a LRG-47cDNA disclosed herein. For example, a derivative of a Tetrahymena L-19 IVS RNA can be constructed in which the nucleotide sequence of the active site is complementary to the nucleotide sequence to be cleaved in an LRG-47-encoding mRNA. See, e.g., Cech et al. U.S. Pat. No. 4,987,071; and Cech et al. U.S. Pat. No. 5,116,742. Alternatively, LRG-47mRNA can be used to select a catalytic RNA having a specific ribonuclease activity from a pool of RNA molecules. See, e.g., Bartel and Szostak (1993) Science 261:1411-1418, incorporated herein by reference.

As used herein, the term "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that flank an ARPKD gene). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Small Interfering RNA

A person of skill in the art can make any number of different siRNAs based on the partial human cDNA gene sequence SEQ ID NO: 1 for LRG-47. When the full gene sequence becomes available, other siRNAs can be designed to block expression, i.e. translation of LRG-47 using routine methods known in the art.

Patent Application 20040023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis and even cell death through apoptosis. Recent work shows that RNA fragments are the sequence-specific mediators of RNAi (Elbashir et al., 2001). Interference of gene expression by these small interfering RNA (siRNA) is now recognized as a naturally occurring strategy for silencing genes in C. elegans, Drosophila, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

In mammalian cell culture, a siRNA-mediated reduction in gene expression has been accomplished by transfecting cells with synthetic RNA nucleic acids (Caplan et al., 2001; Elbashir et al., 2001). The 20040023390 application, the entire contents of which are hereby incorporated by reference as if fully set forth herein, provides methods using a viral vector containing an expression cassette containing a pol II promoter operably-linked to a nucleic acid sequence encoding a small interfering RNA molecule (siRNA) targeted against a gene of interest.

As used herein RNAi is the process of RNA interference. A typical mRNA produces approximately 5,000 copies of a protein. RNAi is a process that interferes with or significantly reduces the number of protein copies made by an mRNA. For example, a double-stranded short interfering RNA (siRNA) molecule is engineered to complement and match the protein-encoding nucleotide sequence of the target mRNA to be interfered with. Following intracellular delivery, the siRNA molecule associates with an RNA-induced silencing complex (RISC). The siRNA-associated RISC binds the target mRNA (such as mRNA encoding LRG-47) through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response.

Methods for Diagnosing MS

Certain other embodiments are also directed to a method for diagnosing multiple sclerosis in an animal preferably a human by assessing the level of human LRG-47 protein in any biological sample taken from the animal, preferably serum, cerebrospinal fluid (CSF) or blood, but also in a tissue sample including fibroblasts or skin.

A method for diagnosing a patient having MS or at risk of developing MS or having MS, involves the steps of a. determining a level of LRG-47 protein in a biological sample taken from the patient and in a corresponding control sample taken from a control subject that is not affected with multiple sclerosis, b. comparing the level of LRG-47 protein in the two biological samples and c. and concluding that the patient has or is at risk of developing multiple sclerosis if the LRG-47 level in the patient sample is significantly higher than the level in the control sample. This method can also be used to detect an autoimmune disease associated with elevated T cells. It is hoped that early detection of changes in LRG-47 expression will facilitate early diagnosis and treatment.

If blood leukocytes or other cells are used in the assay then one can monitor either LRG-47 protein or mRNa levels to make the diagnosis. If the difference between the control and patient levels is very high, and the patient displays other indicia of MS, this test can confirm a diagnosis of MS. Another embodiment is directed to a method for monitoring the level of advancement or progression of MS in a patient by determining changes over time in the LRG-47 protein levels, preferably with regular assessments even during periods of apparent remission. If the level increases over time then the diseases is progressing or becoming more advanced. Monitoring the level of LRG-47 or LRG-47 mRNA in a patient sample can also be sued to measure the efficacy of MS therapy; if the levels are going down the therapy is effective.

The level of LRG-47 may rise before any symptoms of MS have noticeably worsened, making it possible to intervene early in treatment to prevent a serious relapse.

Other embodiments are directed to a diagnostic kit for determining the level of LRG-47 in a biological sample that includes: a) a vessel or vessels for receiving a blood/serum or CSF or cell sample from the subject; b) an agent that specifically detects LRG-47 protein or amplifies LRG-47 mRNA; and c) printed instructions for detecting the LRG-47 protein or the amplified LRG-47 mRNA in the sample. The agent can be a primary anti-LRG-47 antibody for quantifying LRG-47, and a secondary antibody for detecting binding of the primary antibody can also be included in the kit. In another embodiment the antibody is already labeled for easy detection. Any antibody described herein or new antibodies that become known that target LRG-47 can be used, preferably those that target human LRG-47.

Pharmaceutical Preparations

The present invention also includes pharmaceutical compositions and formulations which include the antibodies and antisense compounds of the invention that are administered to treat or prevent multiple sclerosis. The pharmaceutical compositions of the present invention may be administered in a number of ways depending upon whether local or systemic treatment is desired and upon the area to be treated. The preferred rout of administration is intravenous, but administration can also parenteral including intra-arterial, subcutaneous, intraperitoneal or intramuscular injection or infusion; or intracranial, e.g., intrathecal or intraventricular, administration.

Pharmaceutical compositions of the present invention contain the therapeutic agent (antibodies or antisense nucleic acids or si RNA that reduce the expression of LRG-47) in an amount sufficient to prevent or treat MS or an autoimmune disease in a subject. The therapeutic agent can be formulated with an acceptable carrier using methods well known in the art. The actual amount of therapeutic agent will necessarily vary according to the particular formulation, route of administration, and dosage of the pharmaceutical composition, the specific nature of the condition to be treated, and possibly the individual subject. The dosage for the pharmaceutical compositions of the present invention can range broadly depending upon the desired effects, the therapeutic indication, the route of administration, regime, and purity and activity of the composition.

Pharmaceutical compositions of the present invention are suitable for administration to a subject in need of prophylaxis or therapy of MS or an autoimmune disease. The subject is preferably a human but can be non-human as well. A suitable subject can be an individual who is suspected of having, has been diagnosed as having, or is at risk of developing MS or an autoimmune disease, and like conditions as can be determined by one knowledgeable in the art.

Techniques for formulation and administration can be found in "Remington: The Science and Practice of Pharmacy" (20.sup.th edition, Gennaro (ed.) and Gennaro, Lippincott, Williams & Wilkins, 2000), incorporated herein by reference. The pharmaceutical compositions of the present invention can be administered to the subject by a medical device, such as, but not limited to, catheters, balloons, implantable devices, biodegradable implants, prostheses, grafts, sutures, patches, shunts, or stents.

The invention has been described in the foregoing specification with reference to specific embodiments. It will however be evident that various modifications and changes may be made to the embodiments without departing from the broader spirit and scope of the invention. The specification and drawings are to be regarded in an illustrative rather than a restrictive sense.

EXAMPLES

Mice.

LRG-47 knockout mice (LRG-47$^{-/-}$) were generated as described previously [9]. Mice were backcrossed into the B10PL background (N=10 generations). Wild-type (WT) littermates (in B10PL) served as controls.

Induction of EAE.

EAE was induced as previously described [10] using a protocol approved by Columbia University's Institutional Animal Care and Use Committee. Induction of EAE using the MBP model was performed by immunizing B10PL mice subcutaneously with 1-9NAc myelin basic protein (MBP) in complete Freund's adjuvant (CFA) on day 0. For adoptive transfer of EAE, an activated encephalitogenic CD4 Th1 clone (1AE10; 10×10$^6$ cells/animal) was administered intravenously to sublethally irradiated (350 R) mice. Pertussis toxin (100 μg/mouse) was given via the tail vein on days 1 and 3. Clinical symptoms were scored from 1 to 5 as described [10].

Isolation of Mononuclear Cell from the CNS.

To analyze cellular infiltrates in the central nerve system (CNS), mice were deeply anesthetized and perfused intracardially with PBS (30 ml). Brain and spinal cord were chopped into pieces and digested for 45 min at 37° C. in Hanks balanced salt solution containing 0.2 units of liberase R1 (Roche) and 50 μg$^{-1}$ DNase I. Softened tissue fragments were forced through a 40 μm cell strainer, and homogenates were resuspended in 70% Percoll (Sigma) and overlaid with 30% Percoll. Gradients were centrifuged at 2000×g for 30 min. Mononuclear cells in the CNS were collected from the Percoll interface.

Flow Cytometry.

Cells were washed with FACS buffer [PBS containing 0.1% (w/v) sodium azide and 2% (v/v) fetal calf serum] and preincubated with CD16/CD32 monoclonal antibody (clone 2.4G2, Pharmingen) for 15 min at 4° C. to block non-specific binding to Fc receptors. Fluorochrome-conjugated monoclonal antibodies (rat anti-mouse CD4-PerCP, rat anti-mouse CD44-PE and appropriate isotype controls) were purchased from Pharmingen. After incubation, cells were washed twice with FACS buffer and data were acquired on a FACSCalibur flow cytometer (Becton Dickison, Franklin Lakes, N.J.), analyzed by using FLOWJO software (Treestar, San Carlos, Calif.).

Proliferation Assays.

For T-cell proliferation, cells isolated from spleens and lymph nodes were cultured in the serum free medium with 1-9NAc MBP (2.5 μg/ml) for 72 hours. $^3$H-thymindine (1 μCi/well) was added 16 hours prior to harvesting. For the in vivo 5-Bromo-2'-Deoxyuridine (BrdU, Sigma) uptake assay, mice were injected intraperitoneally with 1 mg of BrdU twice on days 13 and 14 during the course of EAE. CNS mononuclear cells were isolated and stained with anti-CD4-PerCP (Pharmingen). BrdU staining was performed according to instructions of the manufacturer (Pharmingen). BrdU incorporation was analyzed on gated CD4$^+$ T cells.

1AE10 Cell Labeling with Carboxyfluorescein Succinimidyl Ester (CFSE) and Assessment of Proliferation.

MBP-specific CD4 T-cell clones (1AE10) were incubated with 2 μM CFSE (Molecular Probes) in T-cell medium for 15 min at 37° C. CFSE staining was stopped by addition of excess medium, and cells were washed twice in medium.

CFSE-labeled 1AE10 cells ($1\times10^6$/ml) were cultured with wild-type spleen cells, the latter as antigen presenting cells (APCs)($2\times10^6$/ml), in T-cell medium containing $MBP_{1-9}$ (2.5 µg/ml) and with/without anti-LRG-47 antibody or non-immune IgG. Cells were harvested at the time points indicated, and stained with anti-CD4-PerCP and anti-CD44-PE IgG. The CFSE fluorescence profile was analyzed on gated $CD4^+$ T-cells.

Assays for Apoptosis.

Apoptosis was measured in vitro using three different methods: (i) The Annexin V assay was used to detect cells in early stages of apoptosis. PI (propidium iodide) staining was detected in the dead cells. 1AE10, splenic and CNS cells were stained with anti-CD4-allophycocyanin and anti-CD44-PE IgG, and resuspended in annexin binding buffer. Cells were stained for 15 min with 5 µl of FITC-labeled annexin V (PharMingen) and 10 µl of PI at room temperature in the dark Analysis was performed by flow cytometry within 1 hr. (ii) In situ detection of apoptotic cells was performed on MBP-activated CD4 T-cells cultured on chamber slides using the in situ Cell Death Detection Kit (Roche, Germany). Briefly, air-dried cell samples were fixed with a freshly prepared fixation solution for 1 h at 15-25° C., and then incubated in permeabilization solution for 2 min on ice. TUNEL-positive cells were detected according to the manufacturer's instructions (Roche, Calif.). The percentage of TUNEL-positive cells is described as the percentage of the number of TUNEL-positive cells divided by the total number of cells in each field.

Quantitative Real-Time PCR.

Total RNA was extracted from 1AE10 cells, lymph nodes and spinal cord using the TRIzol method (Invitrogen Life Technologies) according to the manufacturer's protocol. cDNA synthesis was performed using Random Hexamers primers and the TaqMan Reverse Transcription kit (Applied Biosystems). Samples were subjected to real-time PCR analysis on an ABI Prism 7700 Sequence Detection System under standard conditions. Relative mRNA abundance was normalized against GAPDH (the endogenous control). The primers and probe for LRG were designed using Primer Express software (Applied Biosystems) and purchased from Applied Biosystems (5'-TGG CAA TGG CAT GTC ATC TT-3', reverse primer 5'-AGT ACT CAG TCC GCG TCT TCG T-3', and probe 6FAMACT TCG AGT CAT CGG CMG-BNFQ).

Northern Blotting.

Samples for Northern blotting were collected from 1AE10 cells or MBP-immunized wild-type mice. Total RNA was isolated using Trizol (Invitrogen). For each sample, 5-10 ng of total RNA was electrophoresed through 1% agarose-6% formaldehyde gels. RNAs were transferred to Hybond N+ membranes and hybridized with the $^{32}$P-labeled mouse LRG-47 probes.

ELISA for the Cytokine Detection.

CD4 T-cells were isolated from MBP-immunized mouse spleen/lymph nodes and purified using magnetic beads conjugated with anti-CD4 mAb and a magnetic column (Millen Biotec). 1AE10 cells or CD4 T-cells were cultured in T-cell medium (Click's medium with 10% FCS, 0.01M Hepes, $5\times10^{-5}$ M 2-ME, 8 mM L-glutamine, and antibiotics) at $2\times10^6$/ml (0.5 ml/well) in 48-well plates with MBP (2.5 µg/ml), and irradiated splenic cells ($4\times10^6$/ml) as APCs. Supernatants were collected at the time points indicated. Analyses of murine IFNγ were performed on both supernatants and serum samples, collected at day 14 post induction of EAE using commercially available ELISA kits (R&D Systems, MN). Sensitivity of the assays was <2 pg/ml for IFNγ.

Histology and Immunostaining.

Paraffin-embedded sections were stained with H&E and the area occupied by nuclei per high-power field was evaluated using the Universal Imaging System. To localize LRG-47 antigen in spinal cord, double immunostaining with anti-LRG-47 and anti-CD4 or CD11b IgG was performed. Cryopreserved spinal cord sections were fixed with 4% paraformadehyde in PBS for 30 min. Slides were permeabilized and blocked in PBS containing 5% horse serum and 0.2% saponin for 60 min. They were then incubated with goat anti-LRG-47 IgG (A-19, Santa Cruze, Calif.), rat anti-CD4, or rat anti-CD11b mAbs (BD Pharmingen) followed by secondary antibodies (donkey anti-goat IgG conjugated-FITC and rabbit anti-rat IgG conjugated-TRITC, Sigma). Sections were examined by confocal microscopy.

To localize LRG-47 in MBP-stimulated 1AE10 cells as compared to non-stimulated 1AE10 cells, 1AE10 cells were exposed to MBP (5 µg/ml) for 4 hours, and then were fixed in 4% paraformadehyde alone or plus 0.1% NP-40 for 30 min. Sites of LRG-47 were detected using goat anti-LRG-47 IgG (1:300) followed by donkey anti-goat IgG conjugated with FITC (1:100). To determine the localization of LRG-47 in Golgi apparatus, 1AE10 cells were co-stained with GRASP65 IgG antibody, a maker for the Golgi apparatus (Abcam, Cambridge, Mass.), followed by sheep anti-rabbit IgG conjugated with TRITC (1:200, Sigma, Calif.). Sections were examined by confocal microscopy.

Statistic Analysis.

When two groups were compared, a two-tailed student t-test was used. When multiple groups were compared, analysis of variance (ANOVA) will be employed Fish's t-test was used for post-hoc comparisons. Values of p<0.05 was considered statistically significant.

SiRNA

After stimulated with MBP (5µ/ml) for 48 hour, 1AE10 T cells were transfected with siRNA targeted to mouse LRG-47 (sense sequence: 5'-GGUUACCUGAGGUCAGUAGtt-3', antisense sequence: 5'-CUACUGACCUCAGGUAACCtg-3') using siPORT Amine (Ambion) for additional 24. Levels of LRG-47 mRNA in cells were determined by real-time quantitative PCR and RT-PCR.

Multiple Sclerosis Patient

The spinal cord tissues were obtained from the human Brain and spinal Fluid resource Center, VAMC, Los Angeles, Calif. 90073.

| HSB# | Age | Gender | Neuropathology diagnosis | Coronal Structure |
|---|---|---|---|---|
| 2696 | 86 | F | Multiple Sclerosis | CXL-1 Cervical Cord |
| 2771 | 64 | F | Multiple sclerosis | CXL-1 Cervical Cord |
| 2800 | 64 | F | Multiple Sclerosis | CXL-1 Cervical Cord |
| 2932 | 57 | F | Multiple Sclerosis | CXL-1 Cervical Cord |
| 2935 | 79 | F | Multiple Sclerosis | CXL-1 Cervical Cord |
| 3175 | 54 | F | Normal | CXL-1 Cervical Cord |
| 3216 | 79 | M | Normal Aging | CXL-1 Cervical Cord |
| 3348 | 76 | F | Normal | CXL-1 Cervical Cord |
| 3371 | 52 | M | Normal | CXL-1 Cervical Cord |
| 2348 | 53 | M | Normal | CXL-1 Cervical Cord |

BC128168 Homo sapiens gi:118764008;
Incorporated herein by reference
Partial cDNA sequence (sense strand) for LRG-47
SEQ ID NO: 1
atggaagcca tgaatgttga gaaagcctca gcagatggga
acttgccaga ggtgatctct aacatcaagg agactctgaa

```
gatagtgtcc aggacaccag ttaacatcac tatggcaggg
gactctggca atgggatgtc caccttcatc agtgcccttc
gaaacacagg acatgagggt aaggcctcac ctcctactga
gctggtaaaa gctacccaaa gatgtgcctc ctatttctct
tcccactttt caaatgtggt gttgtgggac ctgcctggca
cagggtctgc caccacaacc ctggagaact acctgatgga
aatgcagttc aaccggtatg acttcatcat ggttgcatct
gcacaattca gcatgaatca tgtgatgctt gccaaaaccg
ctgaggacat gggaaagaag ttctacattg tctggaccaa
gctagacatg gacctcagca caggtgccct cccagaagtg
cagctactgc agatcagaga aaatgtcctg gaaaatctcc
agaaggagcg ggtatgtgaa tactaa BC128168 Homo sapiens gi:118764008
Incorporated herein by reference
AMINO ACID SEQUENCE for LRG-47
                                    SEQ ID NO 2
MNVEKASADGNLPEVISNIKETLKIVSRTPVNITMAGDSGNGMS
TFISALRNTGHEGKASPPTELVKATQRCASYFSSHFSNVVLWDLPGTGSA
TTTLENYLMEMQFNRYDFIMVASAQFSMNHVMLAKTAEDMGKKFYIVWTK
LDMDLSTGALPEVQLLQIRENVLENLQKERVCEY U19119 Mus musculus G-|gi:633753|
Incorporated herein by reference
DNA SEQUENCE FOR for LRG-47.
                                    SEQ ID NO 3
gcaaggtctg ctcgaagacc agaagctgaa agaaaatcca
cgcgatcaga cctcctcttg gttcgtctcc tctcagaagg
actccagacc tctgcatctc atctctcaac atccgggtct
atattccagt tttggatctc tacatag gga acttctgccg
gaggacagca acgttttttgt cctaggaaga aagggggtgac
gttccaggaa ggccactaac atcgaatcac acataataac
tcctctggat cagggtttga ggagtattaa gtgagataag
gcattcgaag gaaccaactc agattcacag acagaggacc
tgtgtgctta aagtctaaga gtggaggaag aacctgagga
gcggcttcct cagagaccct aataaaacca gagagcctca
ccagggagct gaaaggtcca cagacagcgt cactcggatc
ttatcatgaa accatcacac agttcctgcg aggctgctcc
actactcccc aacatggcag agacccatta tgctcccctg
agctcagcct tccccttttgt cacgtcatac caaacaggct
ccagcaggtt acctgaggtc agtaggagca ccgaaagagc
tttaagagaa ggaaaactac tggaactggt ctacggaatc
aaggagactg tggcaacatt gtcccagatt ccagtgagca
tctttgtgac tggggactct ggcaatggca tgtcatcttt
catcaatgca cttcgagtca tcggccatga tgaagatgcc
tcggctccca ctggggtggt gaggaccacg aagacgcgga
ctgagtactc ttcatcccac tttcccaatg tggtgctgtg
ggacttacct ggattggggg ccacagccca aaccgtagag
gactatgtgg aagagatgaa atttagcaca tgtgacttat
tcatcatcat tgcctctgag cagttcagct cgaatcatgt
gaagctgtcc aaaattatcc agagcatggg aaagaggttc
tatattgtct ggaccaagct ggacagggac ctcagcacca
gtgtcctatc agaggtccgg ctcctacaga atatccagga
gaatatccga gagaatctgc agaaggagaa agtgaagtac
ccccccgtgt tcctggtatc cagtctagac cctttactat
atgacttccc gaagcttagg gacacacttc ataaagatct
ctccaacatc aggtgctgtg aacccttaaa gaccctttat
ggcacttatg agaagatcgt tggtgataaa gtagcagtct
ggaagcagag aatagccaac gagtccttga agaattctct
cggtgtcaga gatgatgaca acatgggcga gtgtctgaaa
gtgtaccgac tgatatttgg tgtagatgac gaatcagttc
agcaggtagc ccagagtatg gggacagtag tcatggagta
caaggacaac atgaagtccc aaaactttta tactctccgc
agagaggact ggaaactgag gctgatgaca tgtgcaattg
tgaatgcatt cttccgtttg ttgagatttc tcccatgcgt
atgctgctgt ttaagacgct tgagacataa acgcatgctt
ttcttagttg cccaggacac caagaacatc ctagagaaaa
tcctgaggga ctccatcttc cctccgcaga tctagtataa
gggcagcctg gtaccttct tcttccacag aagccaggtt
accttagatc tctttcctag atccctattt ctccaccaga
aatcaagaga tacaaaaatg cttcctgtaa gggttttaga
ttctctgaga ggagttaaaa tcactcatct cccctgtctc
gattctaatg cattgttcca ctgagggaca gggacaagta
gtgattaaaa ttcattgacc atgattctta gattttgaat
atagaaattt tgtttttggg ctggagagat ggcttagcag
ttaagaacac caactgcttt tccgaaggtc atgagttcaa
atcccagcaa ccacgtgatg gctcacaacc atccgtagtg
agatctgatg ccctcttctg agatgtctga agacagctac
agtgtactta catataataa ataaatatt aaataaataa
```

```
ataaataaat ctttgggaaa aaaattagaa attttgtttt
cagctattaa atgtgatata tgtccaaatc aattttcctc
tgaaacaata aagtcggttc ctcttca
```

U19119 Mus musculus G-|gi:633753|
Incorporated herein by reference
AMINO ACID SEQUENCE FOR LRG-47
                                    SEQ ID NO: 4
MKPSHSSCEAAPLLPNMAETHYAPLSSAFPFVTSYQTGSSRLPE
VSRSTERALREGKLLELVYGIKETVATLSQIPVSIFVTGDSGNGMSSFIN
ALRVIGHDEDASAPTGVVRTTKTRTEYSSSHFPNVVLWDLPGLGATAQTV
EDYVEEMKFSTCDLFIIIASEQFSSNHVKLSKIIQSMGKRFYIVWTKLDR
DLSTSVLSEVRLLQNIQENIRENLQKEKVKYPPVFLVSSLDPLLYDFPKL
RDTLHKDLSNIRCCEPLKTLYGTYEKIVGDKVAVWKQRIANESLKNSLGV
RDDDNMGECLKVYRLIFGVDDESVQQVAQSMGTVVMEYKDNMKSQNFYTL
RREDWKLRLMTCAIVNAFFRLLRFLPCVCCCLRRLRHKRMLFLVAQDTKN
ILEKILRDSIFPPQI

REFERENCES

1. Refaeli, Y., L. Van Parijs, S. I. Alexander, and A. K. Abbas, Interferon gamma is required for activation-induced death of T lymphocytes. J Exp Med, 2002. 196(7): p. 999-1005.
2. Dalton, D. K., L. Haynes, C. Q. Chu, S. L. Swain, and S. Wittmer, Interferon gamma eliminates responding CD4 T cells during mycobacterial infection by inducing apoptosis of activated CD4 T cells. J Exp Med, 2000. 192(1): p. 117-22.
3. Chu, C. Q., S. Wittmer, and D. K. Dalton, Failure to suppress the expansion of the activated CD4 T cell population in interferon gamma-deficient mice leads to exacerbation of experimental autoimmune encephalomyelitis. J Exp Med, 2000. 192(1): p. 123-8.
4. Taylor, G. A., C. G. Feng, and A. Sher, p47 GTPases: regulators of immunity to intracellular pathogens. Nat Rev Immunol, 2004. 4(2): p. 100-9.
5. Taylor, G. A., M. Jeffers, D. A. Largaespada, N. A. Jenkins, N. G. Copeland, and G. F. Woude, Identification of a novel GTPase, the inducibly expressed GTPase, that accumulates in response to interferon gamma. J Biol Chem, 1996. 271(34): p. 20399-405.
6. MacMicking, J. D., IFN-inducible GTPases and immunity to intracellular pathogens. Trends Immunol, 2004. 25(11): p. 601-9.
7. Santiago, H. C., C. G. Feng, A. Bafica, E. Roffe, R. M. Arantes, A. Cheever, G. Taylor, L. Q. Vieira, J. Aliberti, R. T. Gazzinelli, and A. Sher, Mice Deficient in LRG-47 Display Enhanced Susceptibility to *Trypanosoma cruzi* Infection Associated with Defective Hemopoiesis and Intracellular Control of Parasite Growth. J Immunol, 2005. 175 (12): p. 8165-72.
8. Gutierrez, M. G., S. S. Master, S. B. Singh, G. A. Taylor, M. I. Colombo, and V. Deretic, Autophagy is a defense mechanism inhibiting BCG and *Mycobacterium tuberculosis* survival in infected macrophages. Cell, 2004. 119(6): p. 753-66.
9. MacMicking, J. D., G. A. Taylor, and J. D. McKinney, Immune control of tuberculosis by IFN-gamma-inducible LRG-47. Science, 2003. 302(5645): p. 654-9.
10. Yan, S. S., Z. Y. Wu, H. P. Zhang, G. Furtado, X. Chen, S. F. Yan, A. M. Schmidt, C. Brown, A. Stern, J. LaFaille, L. Chess, D. M. Stern, and H. Jiang, Suppression of experimental autoimmune encephalomyelitis by selective blockade of encephalitogenic T-cell infiltration of the central nervous system. Nat Med, 2003. 9(3): p. 287-93.
11. Martens, S., K. Sabel, R. Lange, R. Uthaiah, E. Wolf, and J. C. Howard, Mechanisms regulating the positioning of mouse p47 resistance GTPases LRG-47 and IIGP1 on cellular membranes: retargeting to plasma membrane induced by phagocytosis. J Immunol, 2004. 173(4): p. 2594-606.
12. Butcher, B. A., R. I. Greene, S. C. Henry, K. L. Annecharico, J. B. Weinberg, E. Y. Denkers, A. Sher, and G. A. Taylor, p47 GTPases regulate Toxoplasma gondii survival in activated macrophages. Infect Immun, 2005. 73(6): p. 3278-86.
13. MacMicking, J. D., Immune control of phagosomal bacteria by p47 GTPases. Curr Opin Microbiol, 2005. 8(1): p. 74-82.
14. Feng, C. G., C. M. Collazo-Custodio, M. Eckhaus, S. Hieny, Y. Belkaid, K. Elkins, D. Jankovic, G. A. Taylor, and A. Sher, Mice deficient in LRG-47 display increased susceptibility to mycobacterial infection associated with the induction of lymphopenia. J Immunol, 2004. 172(2): p. 1163-8.
15. Sorace, J. M., R. J. Johnson, D. L. Howard, and B. E. Drysdale, Identification of an endotoxin and IFN-inducible cDNA: possible identification of a novel protein family. J Leukoc Biol, 1995. 58(4): p. 477-84.
16. Collazo, C. M., G. S. Yap, G. D. Sempowski, K. C. Lusby, L. Tessarollo, G. F. Woude, A. Sher, and G. A. Taylor, Inactivation of LRG-47 and IRG-47 reveals a family of interferon gamma-inducible genes with essential, pathogen-specific roles in resistance to infection. J Exp Med, 2001. 194(2): p. 181-8.
17. O'Connor, R. A., S. Wittmer, and D. K. Dalton, Infection-induced apoptosis deletes bystander CD4+ T cells: a mechanism for suppression of autoimmunity during BCG infection. J Autoimmun, 2005. 24(2): p. 93-100.
18. Zhang, Y., J. N. Blattman, N. J. Kennedy, J. Duong, T. Nguyen, Y. Wang, R. J. Davis, P. D. Greenberg, R. A. Flavell, and C. Dong, Regulation of innate and adaptive immune responses by MAP kinase phosphatase 5. Nature, 2004. 430(7001): p. 793-7.

---

What is claimed is:

1. A method for treating a T-cell mediated autoimmune disease selected from the group consisting of EAE and ADEM, in a patient, comprising administering a therapeutically effective amount of an isolated anti-LRG-47 antibody or biologically active fragment that binds LRG-47.

2. The method of claim 1, wherein the isolated antibody is polyclonal anti-human LRG-47 antibody 138AB or a biologically active fragment that binds LRG-47.

3. The method of claim 1, wherein the isolated anti-LRG-47 antibody is a humanized antibody selected from the group comprising LRG-47 (A-19) antibody, LRG-47 (M-95) antibody, LRG-47 (M-16) antibody, and LRG-47 (P-20) antibody, or biologically active fragment that binds LRG-47.

4. The method of claim 1, wherein the isolated antibody is a monoclonal, polyclonal, chimeric, humanized or bispecific antibody.

* * * * *

SEQUENCE LISTING

```
<160> NUMBER OF SEQ ID NOS: 8

<210> SEQ ID NO 1
<211> LENGTH: 546
<212> TYPE: DNA
<213> ORGANISM: Homo sapiens

<400> SEQUENCE: 1
atggaagcca tgaatgttga gaaagcctca gcagatggga acttgccaga ggtgatctct      60
aacatcaagg agactctgaa gatagtgtcc aggacaccag ttaacatcac tatggcaggg     120
gactctggca atgggatgtc caccttcatc agtgcccttc gaaacacagg acatgagggt     180
aaggcctcac ctcctactga gctggtaaaa gctacccaaa gatgtgcctc ctatttctct     240
tcccactttt caaatgtggt gttgtgggac ctgcctggca cagggtctgc caccacaacc     300
ctggagaact acctgatgga aatgcagttc aaccggtatg acttcatcat ggttgcatct     360
gcacaattca gcatgaatca tgtgatgctt gccaaaaccg ctgaggacat gggaaagaag     420
ttctacattg tctggaccaa gctagacatg gacctcagca caggtgccct cccagaagtg     480
cagctactgc agatcagaga aaatgtcctg gaaaatctcc agaaggagcg ggtatgtgaa     540
tactaa                                                                546

<210> SEQ ID NO 2
<211> LENGTH: 178
<212> TYPE: PRT
<213> ORGANISM: Homo sapiens

<400> SEQUENCE: 2

Met Asn Val Glu Lys Ala Ser Ala Asp Gly Asn Leu Pro Glu Val Ile
1               5                   10                  15

Ser Asn Ile Lys Glu Thr Leu Lys Ile Val Ser Arg Thr Pro Val Asn
            20                  25                  30

Ile Thr Met Ala Gly Asp Ser Gly Asn Gly Met Ser Thr Phe Ile Ser
        35                  40                  45

Ala Leu Arg Asn Thr Gly His Glu Gly Lys Ala Ser Pro Pro Thr Glu
    50                  55                  60

Leu Val Lys Ala Thr Gln Arg Cys Ala Ser Tyr Phe Ser Ser His Phe
65                  70                  75                  80

Ser Asn Val Val Leu Trp Asp Leu Pro Gly Thr Gly Ser Ala Thr Thr
                85                  90                  95
```

```
Thr Leu Glu Asn Tyr Leu Met Glu Met Gln Phe Asn Arg Tyr Asp Phe
            100                 105                 110

Ile Met Val Ala Ser Ala Gln Phe Ser Met Asn His Val Met Leu Ala
        115                 120                 125

Lys Thr Ala Glu Asp Met Gly Lys Lys Phe Tyr Ile Val Trp Thr Lys
130                 135                 140

Leu Asp Met Asp Leu Ser Thr Gly Ala Leu Pro Glu Val Gln Leu Leu
145                 150                 155                 160

Gln Ile Arg Glu Asn Val Leu Glu Asn Leu Gln Lys Glu Arg Val Cys
                165                 170                 175

Glu Tyr

<210> SEQ ID NO 3
<211> LENGTH: 2227
<212> TYPE: DNA
<213> ORGANISM: Mus musculus

<400> SEQUENCE: 3
gcaaggtctg ctcgaagacc agaagctgaa agaaaatcca cgcgatcaga cctcctcttg      60
gttcgtctcc tctcagaagg actccagacc tctgcatctc atctctcaac atccgggtct    120
atattccagt tttggatctc tacataggga acttctgccg gaggacagca acgttttttgt    180 cctaggaaga aaggggtgac gttccaggaa ggccactaac atcgaatcac acataataac    240
tcctctggat cagggtttga ggagtattaa gtgagataag gcattcgaag gaaccaactc    300
agattcacag acagaggacc tgtgtgctta agtctaagaa gtggaggaag aacctgagga    360
gcggcttcct cagagaccct aataaaacca gagagcctca ccagggagct gaaaggtcca    420
cagacagcgt cactcggatc ttatcatgaa accatcacac agttcctgcg aggctgctcc    480
actactcccc aacatggcag agacccatta tgctcccctg agctcagcct tccccttttgt    540 cacgtcatac caaacaggct ccagcaggtt acctgaggtc agtaggagca ccgaaagagc    600
tttaagagaa ggaaaactac tggaactggt ctacggaatc aaggagactg tggcaacatt    660
gtcccagatt ccagtgagca tctttgtgac tggggactct ggcaatggca tgtcatcttt    720
catcaatgca cttcgagtca tcggccatga tgaagatgcc tcggctccca ctggggtggt    780
gaggaccacg aagacgcgga ctgagtactc ttcatcccac tttcccaatg tggtgctgtg    840
ggacttacct ggattggggg ccacagccca aaccgtagag gactatgtgg aagagatgaa    900
atttagcaca tgtgacttat tcatcatcat tgcctctgag cagttcagct cgaatcatgt    960
gaagctgtcc aaaattatcc agagcatggg aaagaggttc tatattgtct ggaccaagct   1020
ggacagggac ctcagcacca gtgtcctatc agaggtccgg ctcctacaga atatccagga   1080
gaatatccga gagaatctgc agaaggagaa agtgaagtac cccccgtgt tcctggtatc   1140 cagtctagac cctttactat atgacttccc gaagcttagg gacacacttc ataaagatct   1200
ctccaacatc aggtgctgtg aacccttaaa gaccctttat ggcacttatg gaagatcgt   1260 tggtgataaa gtagcagtct ggaagcagag aatagccaac gagtccttga agaattctct   1320
cggtgtcaga gatgatgaca acatgggcga gtgtctgaaa gtgtaccgac tgatatttgg   1380
tgtagatgac gaatcagttc agcaggtagc ccagagtatg gggacagtag tcatggagta   1440
caaggacaac atgaagtccc aaaacttttta tactctccgc agagaggact ggaaactgag   1500
gctgatgaca tgtgcaattg tgaatgcatt cttccgtttg ttgagatttc tcccatgcgt   1560
atgctgctgt ttaagacgct tgagacataa acgcatgctt tcttagttg cccaggacac   1620
```

```
caagaacatc ctagagaaaa tcctgaggga ctccatcttc cctccgcaga tctagtataa    1680
gggcagcctg gtaccttct tcttccacag aagccaggtt accttagatc tctttcctag      1740
atccctattt ctccaccaga aatcaagaga tacaaaaatg cttcctgtaa gggttttaga    1800
ttctctgaga ggagttaaaa tcactcatct cccctgtctc gattctaatg cattgttcca    1860
ctgagggaca gggacaagta gtgattaaaa ttcattgacc atgattctta gatttggaat    1920
atagaaattt tgttttgggg ctggagagat ggcttagcag ttaagaacac caactgcttt    1980
tccgaaggtc atgagttcaa atcccagcaa ccacgtgatg gctcacaacc atccgtagtg    2040
agatctgatg ccctcttctg agatgtctga agacagctac agtgtactta catataataa    2100
ataaataaat aaataaataa ataaataaat ctttgggaaa aaaattagaa attttgtttt    2160
cagctattaa atgtgatata tgtccaaatc aatttcctc tgaaacaata aagtcggttc     2220
ctcttca                                                                2227
```

<210> SEQ ID NO 4
<211> LENGTH: 409
<212> TYPE: PRT
<213> ORGANISM: Mus musculus

<400> SEQUENCE: 4

```
Met Lys Pro Ser His Ser Ser Cys Glu Ala Ala Pro Leu Leu Pro Asn
1               5                   10                  15

Met Ala Glu Thr His Tyr Ala Pro Leu Ser Ser Ala Phe Pro Phe Val
            20                  25                  30

Thr Ser Tyr Gln Thr Gly Ser Ser Arg Leu Pro Glu Val Ser Arg Ser
        35                  40                  45

Thr Glu Arg Ala Leu Arg Glu Gly Lys Leu Leu Glu Leu Val Tyr Gly
    50                  55                  60

Ile Lys Glu Thr Val Ala Thr Leu Ser Gln Ile Pro Val Ser Ile Phe
65                  70                  75                  80

Val Thr Gly Asp Ser Gly Asn Gly Met Ser Ser Phe Ile Asn Ala Leu
                85                  90                  95

Arg Val Ile Gly His Asp Glu Asp Ala Ser Ala Pro Thr Gly Val Val
            100                 105                 110

Arg Thr Thr Lys Thr Arg Thr Glu Tyr Ser Ser Ser His Phe Pro Asn
        115                 120                 125

Val Val Leu Trp Asp Leu Pro Gly Leu Gly Ala Thr Ala Gln Thr Val
    130                 135                 140

Glu Asp Tyr Val Glu Glu Met Lys Phe Ser Thr Cys Asp Leu Phe Ile
145                 150                 155                 160

Ile Ile Ala Ser Glu Gln Phe Ser Ser Asn His Val Lys Leu Ser Lys
                165                 170                 175

Ile Ile Gln Ser Met Gly Lys Arg Phe Tyr Ile Val Trp Thr Lys Leu
            180                 185                 190

Asp Arg Asp Leu Ser Thr Ser Val Leu Ser Glu Val Arg Leu Leu Gln
        195                 200                 205

Asn Ile Gln Glu Asn Ile Arg Glu Asn Leu Gln Lys Glu Lys Val Lys
    210                 215                 220

Tyr Pro Pro Val Phe Leu Val Ser Ser Leu Asp Pro Leu Leu Tyr Asp
225                 230                 235                 240

Phe Pro Lys Leu Arg Asp Thr Leu His Lys Asp Leu Ser Asn Ile Arg
                245                 250                 255

Cys Cys Glu Pro Leu Lys Thr Leu Tyr Gly Thr Tyr Glu Lys Ile Val
```

```
                    260                 265                 270
Gly Asp Lys Val Ala Val Trp Lys Gln Arg Ile Ala Asn Glu Ser Leu
            275                 280                 285

Lys Asn Ser Leu Gly Val Arg Asp Asp Asn Met Gly Glu Cys Leu
        290                 295                 300

Lys Val Tyr Arg Leu Ile Phe Gly Val Asp Asp Glu Ser Val Gln Gln
305                 310                 315                 320

Val Ala Gln Ser Met Gly Thr Val Val Met Glu Tyr Lys Asp Asn Met
                325                 330                 335

Lys Ser Gln Asn Phe Tyr Thr Leu Arg Arg Glu Asp Trp Lys Leu Arg
            340                 345                 350

Leu Met Thr Cys Ala Ile Val Asn Ala Phe Phe Arg Leu Leu Arg Phe
        355                 360                 365

Leu Pro Cys Val Cys Cys Leu Arg Arg Leu Arg His Lys Arg Met
        370                 375                 380

Leu Phe Leu Val Ala Gln Asp Thr Lys Asn Ile Leu Glu Lys Ile Leu
385                 390                 395                 400

Arg Asp Ser Ile Phe Pro Pro Gln Ile
                405

<210> SEQ ID NO 5
<211> LENGTH: 19
<212> TYPE: RNA
<213> ORGANISM: Mus musculus

<400> SEQUENCE: 5
gguuaccuga ggucaguag                                              19

<210> SEQ ID NO 6
<211> LENGTH: 19
<212> TYPE: RNA
<213> ORGANISM: Mus musculus

<400> SEQUENCE: 6
cuacugaccu cagguaacc                                              19

<210> SEQ ID NO 7
<211> LENGTH: 19
<212> TYPE: PRT
<213> ORGANISM: Artificial Sequence
<220> FEATURE:
<223> OTHER INFORMATION: Synthetic Construct

<400> SEQUENCE: 7

Val Gly His Glu Gly Lys Ala Ser Pro Pro Thr Glu Leu Val Lys Ala
1               5                   10                  15

Thr Gln Arg

<210> SEQ ID NO 8
<211> LENGTH: 19
<212> TYPE: PRT
<213> ORGANISM: Artificial Sequence
<220> FEATURE:
<223> OTHER INFORMATION: Synthetic Construct

<400> SEQUENCE: 8

Glu Asp Met Gly Lys Lys Phe Tyr Ile Val Trp Thr Lys Leu Asp Met
1               5                   10                  15

Asp Leu Cys
```